(12) United States Patent
Shiomi et al.

(10) Patent No.: US 10,461,258 B2
(45) Date of Patent: Oct. 29, 2019

(54) COMPOUND

(71) Applicant: IDEMITSU KOSAN CO., LTD., Tokyo (JP)

(72) Inventors: Takushi Shiomi, Sodegaura (JP); Masahiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 374 days.

(21) Appl. No.: 15/389,912

(22) Filed: Dec. 23, 2016

(65) Prior Publication Data

US 2017/0186968 A1    Jun. 29, 2017

(30) Foreign Application Priority Data

Dec. 24, 2015   (JP) .................. 2015-252200
Mar. 29, 2016   (JP) .................. 2016-065382

(51) Int. Cl.
| | |
|---|---|
| *H01L 51/00* | (2006.01) |
| *C07D 401/10* | (2006.01) |
| *C07D 401/14* | (2006.01) |
| *C07D 251/24* | (2006.01) |
| *C07D 405/10* | (2006.01) |
| *H01L 51/50* | (2006.01) |

(52) U.S. Cl.
CPC ........ *H01L 51/0067* (2013.01); *C07D 251/24* (2013.01); *C07D 401/10* (2013.01); *C07D 401/14* (2013.01); *C07D 405/10* (2013.01); *H01L 51/0055* (2013.01); *H01L 51/0072* (2013.01); *H01L 51/0073* (2013.01); *H01L 51/0077* (2013.01); *H01L 51/508* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5076* (2013.01); *H01L 51/5092* (2013.01)

(58) Field of Classification Search
CPC .................................................. H01L 51/0055
See application file for complete search history.

(56) References Cited

U.S. PATENT DOCUMENTS

| | | |
|---|---|---|
| 2011/0288292 A1 | 11/2011 | Parham et al. |
| 2012/0132899 A1 | 5/2012 | Kawamura et al. |
| 2012/0214993 A1 | 8/2012 | Aihara et al. |
| 2014/0114076 A1 | 4/2014 | Parham et al. |
| 2014/0330013 A1 | 11/2014 | Aihara et al. |
| 2015/0318486 A1 | 11/2015 | Kim et al. |
| 2015/0329544 A1 | 11/2015 | Aihara et al. |
| 2018/0351108 A1* | 12/2018 | Moon ............... H01L 51/0052 |

FOREIGN PATENT DOCUMENTS

| | | | |
|---|---|---|---|
| CN | 105924383 A | 9/2016 | |
| JP | 2012-515730 A | 7/2012 | |
| WO | WO 2010/083869 A2 | 7/2010 | |
| WO | WO-2011/021689 A1 | 2/2011 | |
| WO | WO-2011/086935 A1 | 7/2011 | |
| WO | WO-2011157779 A1 * | 12/2011 | ........... C07D 401/14 |
| WO | WO-2013/069762 A1 | 5/2013 | |
| WO | WO-2015/008866 A1 | 1/2015 | |
| WO | WO 2016/175292 A1 | 11/2016 | |

OTHER PUBLICATIONS

International Search Report dated Mar. 28, 2017 in PCT/JP20156/088408.

* cited by examiner

*Primary Examiner* — Peter F Godenschwager
(74) *Attorney, Agent, or Firm* — Foley & Lardner LLP

(57) ABSTRACT

A compound represented by the following formula (1):

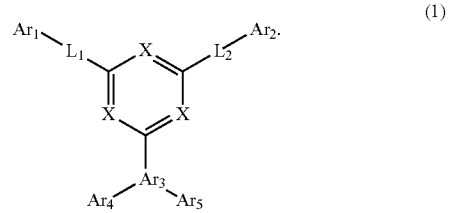

19 Claims, No Drawings

COMPOUND

TECHNICAL FIELD

The invention relates to a novel compound and to an organic electroluminescence device and an electronic apparatus using the same.

BACKGROUND ART

An organic electroluminescence (EL) device is regarded as a promising solid-emitting inexpensive large-area full color display device, and various developments have been conducted so far. In general, an organic EL device comprises an emitting layer and a pair of opposing electrodes that sandwich the emitting layer. When an electrical field is applied between the both electrodes, electrons are injected from the cathode and holes are injected from the anode. Further, these electrons are re-combined with the holes in the emitting layer, create an excited state, and energy is emitted as light when the excited state is returned to the ground state.

Conventional organic EL devices have a problem that they are insufficient in respect of device lifetime. Prolonging the lifetime of an organic EL device is an important subject, and hence, materials for an organic EL devices have been gradually improved in recent years (Patent Documents 1 to 3, for example). However, further prolongation of the lifetime has been demanded.

RELATED ART DOCUMENTS

Patent Documents

Patent Document 1: WO2011/021689 pamphlet
Patent Document 2: WO2013/069762 pamphlet
Patent Document 3: WO2015/008866 pamphlet

SUMMARY OF THE INVENTION

Problems to be Solved by the Invention

An object of the invention is to provide a compound capable of prolonging the lifetime of an organic electroluminescence device.

Means for Solving the Problem

According to one aspect of the invention, the following compounds or the like are provided.
A compound represented by the following formula (1):

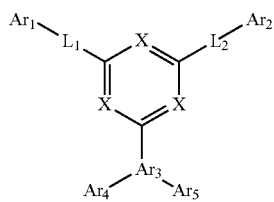

wherein in the formula (1), Xs are independently a nitrogen atom or CH, and at least two Xs are nitrogen atoms;
$Ar_1$ and $Ar_2$ are independently a substituted or unsubstituted aromatic hydrocarbon group including 6 to 30 carbon atoms that form a ring (hereinafter referred to as "ring carbon atoms") or a substituted or unsubstituted aromatic heterocyclic group including 5 to 30 atoms that form a ring (hereinafter referred to as "ring atoms");
$L_1$ and $L_2$ are independently a single bond or a substituted or unsubstituted divalent aromatic hydrocarbon group including 6 to 30 ring carbon atoms;
$Ar_3$ is a substituted or unsubstituted aromatic hydrocarbon group including 6 to 15 ring carbon atoms;
$Ar_4$ is a substituted or unsubstituted 6-membered nitrogen-containing aromatic monocyclic group or a substituted or unsubstituted nitrogen-containing aromatic fused ring group in which two or more 6-membered rings are fused; and
$Ar_5$ is a substituted or unsubstituted aromatic hydrocarbon fused ring group including 20 to 50 ring carbon atoms or a substituted or unsubstituted nitrogen-containing aromatic fused ring group including 20 to 50 ring atoms.

Advantageous Effects of the Invention

According to the invention, it is possible to provide a compound capable of prolonging the lifetime of an organic electroluminescence device.

MODE FOR CARRYING OUT THE INVENTION

[Novel Compound]
The compound according to one aspect of the invention is represented by the following formula (1):

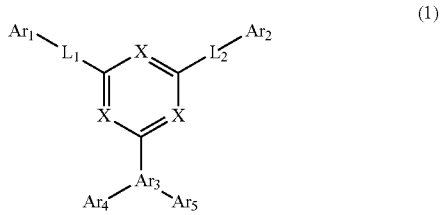

wherein in the formula (1), Xs are independently a nitrogen atom or CH, and at least two Xs are nitrogen atoms;
$Ar_1$ and $Ar_2$ are independently a substituted or unsubstituted aromatic hydrocarbon group including 6 to 30 ring carbon atoms or a substituted or unsubstituted aromatic heterocyclic group including 5 to 30 ring atoms;
$L_1$ and $L_2$ are independently a single bond or a substituted or unsubstituted divalent aromatichydrocarbon group including 6 to 30 ring carbon atoms;
$Ar_3$ is a substituted or unsubstituted aromatic hydrocarbon group including 6 to 15 ring carbon atoms;
$Ar_4$ is a substituted or unsubstituted 6-membered nitrogen-containing aromatic monocyclic group or a substituted or unsubstituted nitrogen-containing aromatic fused ring group in which two or more 6-membered rings are fused; and
$Ar_5$ is a substituted or unsubstituted aromatic hydrocarbon fused ring group including 20 to 50 ring carbon atoms or a substituted or unsubstituted nitrogen-containing aromatic fused ring group including 20 to 50 ring atoms.

Due to the above-mentioned structure, when the compound according to one aspect of the present invention is used in an organic EL device, it can prolong the lifetime thereof.

In the formula (1), as $Ar_3$, a group corresponding to a substituted or unsubstituted benzene ring, a group corresponding to a substituted or unsubstituted naphthalene ring, a group corresponding to a substituted or unsubstituted anthracene ring or the like can be given. A group corresponding to a substituted or unsubstituted benzene ring is preferable. The compound according to one aspect of the invention is preferably represented by the following formula (2):

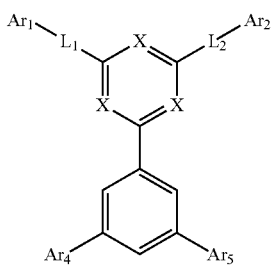

wherein in the formula (2), X, $Ar_1$, $Ar_2$, $L_1$, $L_2$, $Ar_4$ and $Ar_5$ are as defined in the formula (1).

In the formula (1), $Ar_5$ is preferably a 5-membered aromatic hydrocarbon fused ring group in which five rings are fused or a 5-membered nitrogen-containing aromatic fused ring group in which five rings are fused. $Ar_5$ may have a substituent. The 5-membered fused ring is preferably a fused ring in which five 6-membered aromatic rings are fused.

$Ar_5$ is preferably represented by any of the following formulas (11) to (13):

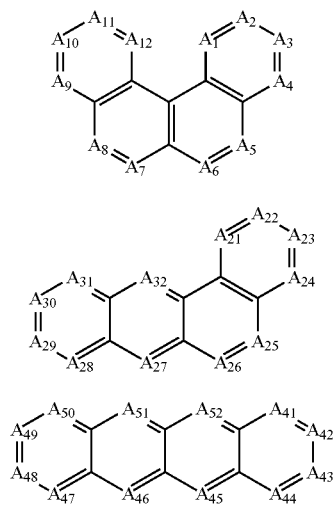

In the formula (11), any one of $A_1$ to $A_{12}$ is a carbon atom that is used for bonding with $Ar_3$, and any adjacent two of $A_1$ to $A_{12}$ that are not used for bonding with $Ar_3$ are $CR_1$s. The two $R_1$s are bonded with each other to form a substituted or unsubstituted 6-membered ring, and remaining $A_1$ to $A_{12}$ are independently a nitrogen atom or $CR_2$.

The two $R_1$s may independently be a substituent capable of forming a substituted or unsubstituted 6-membered ring by bonding with each other. The two $R_1$s may be the same as or different from each other.

$R_2$ is a hydrogen atom or a substituent.

In the formula (12), any one of $A_{21}$ to $A_{32}$ is a carbon atom that is used for bonding with $Ar_3$, any adjacent two of $A_{21}$ to $A_{32}$ that are not used for bonding with $Ar_3$ are $CR_1$s, the two $R_1$s are bonded with each other to form a substituted or unsubstituted 6-membered ring, and remaining $A_{21}$ to $A_{32}$ are independently a nitrogen atom or $CR_2$.

In the formula (13), any one of $A_{41}$ to $A_{52}$ is a carbon atom that is used for bonding with $Ar_3$, any adjacent two of $A_{41}$ to $A_{52}$ that are not used for bonding with $Ar_3$ are $CR_1$s, the two $R_1$s are bonded with each other to form a substituted or unsubstituted 6-membered ring, and remaining $A_{41}$ to $A_{52}$ are independently a nitrogen atom or $CR_2$.

$Ar_5$ is preferably represented by any of the following formulas (21) to (24):

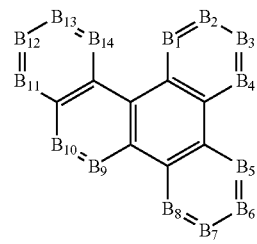

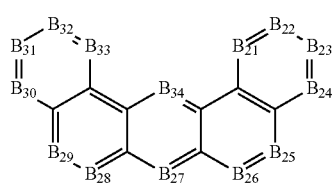

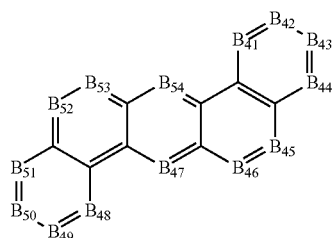

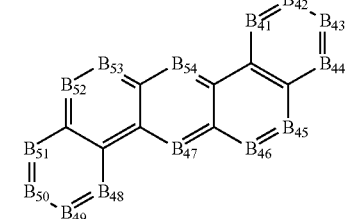

In the formula (21), any one of $B_1$ to $B_{14}$ is a carbon atom that is used for bonding with $Ar_3$, and $B_1$ to $B_{14}$ that are not used for bonding with $Ar_3$ are independently a nitrogen atom or $CR_{11}$.

$R_{11}$ is a hydrogen atom or a substituent.

In the formula (22), any one of $B_{21}$ to $B_{34}$ is a carbon atom that is used for bonding with $Ar_3$, and $B_{21}$ to $B_{34}$ that are not used for bonding with $Ar_3$ are independently a nitrogen atom or $CR_{11}$.

In the formula (23), any one of $B_{41}$ to $B_{54}$ is a carbon atom that is used for bonding with $Ar_3$, and $B_{41}$ to $B_{54}$ that are not used for bonding with $Ar_3$ are independently a nitrogen atom or $CR_{11}$.

In the formula (24), any one of $B_{61}$ to $B_{73}$ are a carbon atom that is used for bonding with $Ar_3$, and $B_{61}$ to $B_{73}$ that are not used for bonding with $Ar_3$ are independently a nitrogen atom or $CR_{11}$.

Ar$_5$ is preferably represented by any of the following formulas (31) to (37), and more preferably is represented by formula (31):

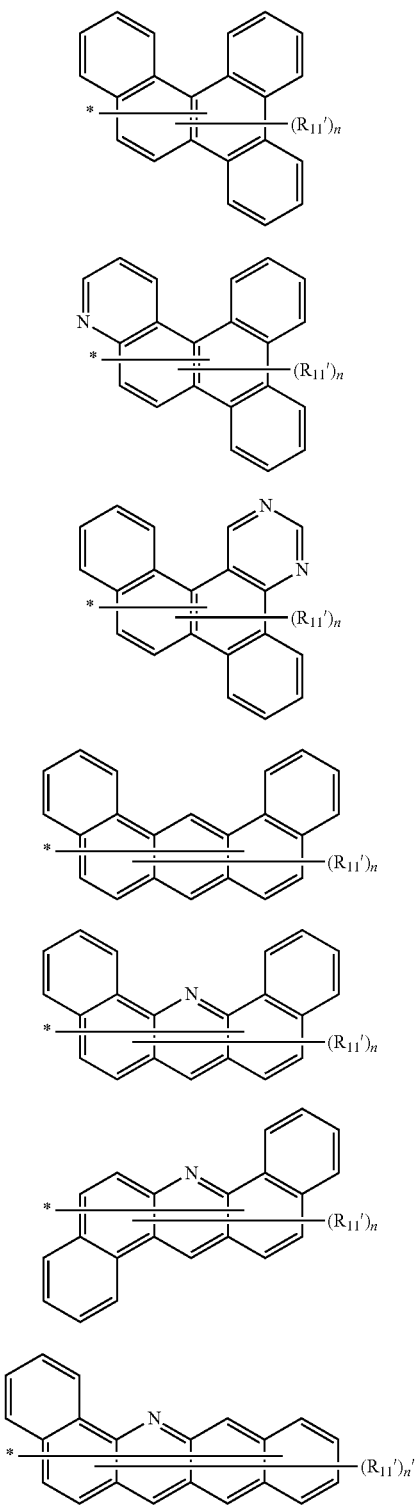

wherein in the formulas (31) to (37), R$_{11}$' is a substituent, n is an integer of 0 to 13, n' is an integer of 0 to 12, and * is a bonding position with Ar$_3$. R$_{11}$' may be bonded to any position of the fused ring. The bonding position with Ar$_3$ may be any position of the fused ring.

In the formula (1), as examples of Ar$_4$, those represented by any of the following formulas can be given.

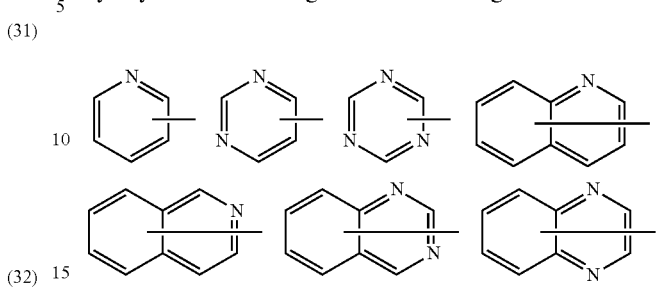

Ar$_4$ is preferably represented by any of the following formulas:

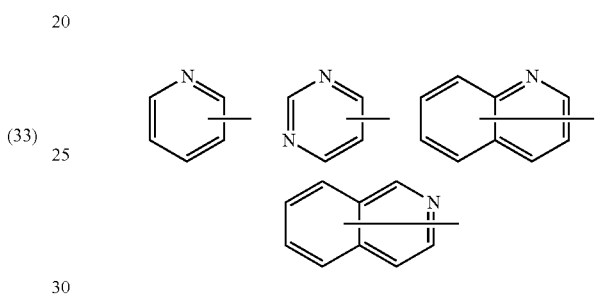

In the formula (1), it is preferred that Ar$_1$ and Ar$_2$ be independently a substituted or unsubstituted aromatic hydrocarbon group including 6 to 30 ring carbon atoms. More preferably, Ar$_1$ and Ar$_2$ are independently a substituted or unsubstituted phenyl group, a substituted or unsubstituted biphenyl group, a substituted or unsubstituted naphthyl group or a substituted or unsubstituted fluorenyl group.

In the formula (1), it is preferred that L$_1$ and L$_2$ be independently a single bond or a substituted or unsubstituted phenylene group.

In the formula (1), it is preferred that any of the three Xs be a nitrogen atom.

The compound according to one aspect of the invention is preferably represented by any of the following formulas:

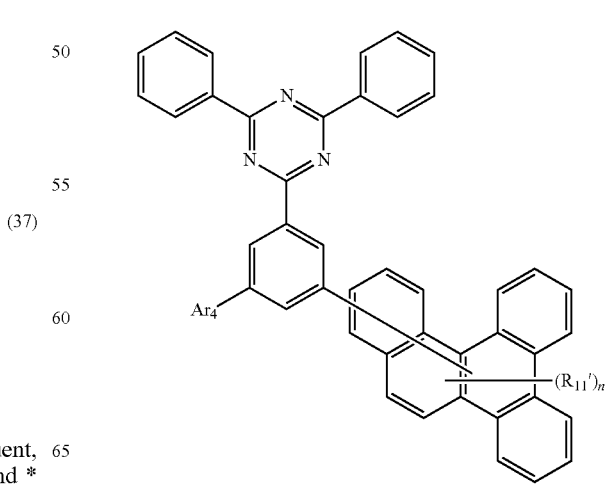

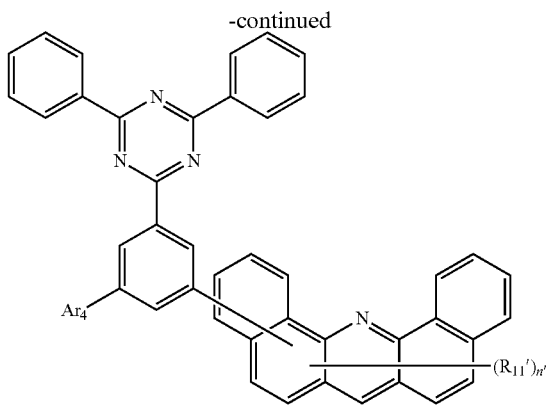

wherein in the formulas, $Ar_4$, $R_{11}'$, n and n' are as mentioned above. The bonding position with the benzene ring may be any position of the fused ring.

The above-mentioned compound can be produced by a method described in the Examples. Further, in accordance with this reaction, the compound of the invention can be synthesized by using a known alternative reaction or raw materials suitable for an intended product.

In the invention, a hydrogen atom includes isomers differing in number of neutrons, i.e. protium, deuterium and tritium.

In the present specification, the number of "ring carbon atoms" means the number of carbon atoms among atoms constituting a ring of a compound in which atoms are bonded in the form of a ring (for example, a monocyclic compound, a fused ring compound, a cross-linked compound, a carbocyclic compound or a heterocyclic compound). When the ring is substituted by a substituent, the carbon contained in the substituent is not included in the number of ring carbon atoms. The same is applied to the "ring carbon atoms" mentioned below, unless otherwise indicated. For example, a benzene ring includes 6 ring carbon atoms, a naphthalene ring includes 10 ring carbon atoms, a pyridinyl group includes 5 ring carbon atoms, and a furanyl group includes 4 ring carbon atoms. When a benzene ring or a naphthalene ring is substituted by an alkyl group as a substituent, for example, the number of carbon atoms of the alkyl group is not included in the number of ring carbon atoms. When a fluorene ring is bonded with a fluorene ring as a substituent (including a spirofluorene ring), for example, the number of carbon atoms of the fluorene ring as a substituent is not included in the number of ring carbon atoms.

In the present specification, the number of the "ring atoms" means the number of atoms constituting a ring of a compound in which atoms are bonded in the form of a ring (for example, a monocycle, a fused ring or a ring assembly) (for example, a monocyclic compound, a fused ring compound, a cross-linked compound, a carbocyclic compound or a heterocyclic compound). Atoms that do not constitute a ring or atoms included in a substituent by which the ring is substituted are not included in the number of ring atoms. The same is applied to the number of the "ring atoms" mentioned below, unless otherwise indicated. For example, a pyridine ring includes 6 ring atoms, a quinazoline ring includes 10 ring atoms and a furan ring includes 5 ring atoms. The hydrogen atom bonded with the carbon atom of the pyridine ring or the quinazoline ring, respectively, or atoms that constitute a substituent are not included in number of the ring atoms. When a fluorene ring is bonded with a fluorene ring as a substituent (including a spirofluorene ring, for example), the number of atoms of the fluorene ring as a substituent is not included in the number of ring atoms.

In the present specification, the "XX to YY carbon atoms" in the "substituted or unsubstituted ZZ group including XX to YY carbon atoms" means the number of carbon atoms when the ZZ group is unsubstituted. The number of carbon atoms of a substituent when the group is substituted is not included.

In the present specification, the "XX to YY atoms" in the "substituted or unsubstituted ZZ group including XX to YY atoms" means the number of atoms when the ZZ group is unsubstituted. The number of atoms of a substituent when the group is substituted is not included.

In the present specification, the "unsubstituted" in the "substituted or unsubstituted" means bonding of a hydrogen atom, not substitution by the substituent mentioned above.

An explanation will be given on specific examples of each group in each formula".

As examples of the aromatic hydrocarbon group (aryl group), a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenylyl group, a terphenyl group, a fluoranthenyl group, a spirofluorene group or the like can be given, for example.

It is preferred that the aromatic hydrocarbon group have 6 to 20, more preferably 6 to 12, ring carbon atoms. As one preferable aspect of the aromatic hydrocarbon group, a phenyl group, a naphthyl group, a phenanthryl group or the like can be given.

As for the divalent or higher valent aromatic hydrocarbon group, divalent or higher valent groups corresponding to the groups exemplified above as the example of the aryl group can be given.

As the aromatic heterocyclic group (heteroaryl group), a pyrrolyl group, a triazinyl group, a pyrazinyl group, a pyrimidinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiophenyl group, a quinazolinyl group, a benzimidazolyl group or the like can be given, for example.

The number of ring atoms of the aromatic heterocyclic group is preferably 5 to 20, with 5 to 14 being further preferable. As one preferable aspect of the aromatic heterocyclic group, a triazinyl group, a pyrimidinyl group, a pyridinyl group, a dibenzofuranyl group, a dibenzothiophenyl group, a carbazolyl group or the like can be given, for example.

As for the divalent or higher valent aromatic heterocyclic group, divalent or higher valent groups corresponding to the groups exemplified above as the example of the heteroaryl group can be given.

The above-mentioned "carbazolyl group" also includes the following structures.

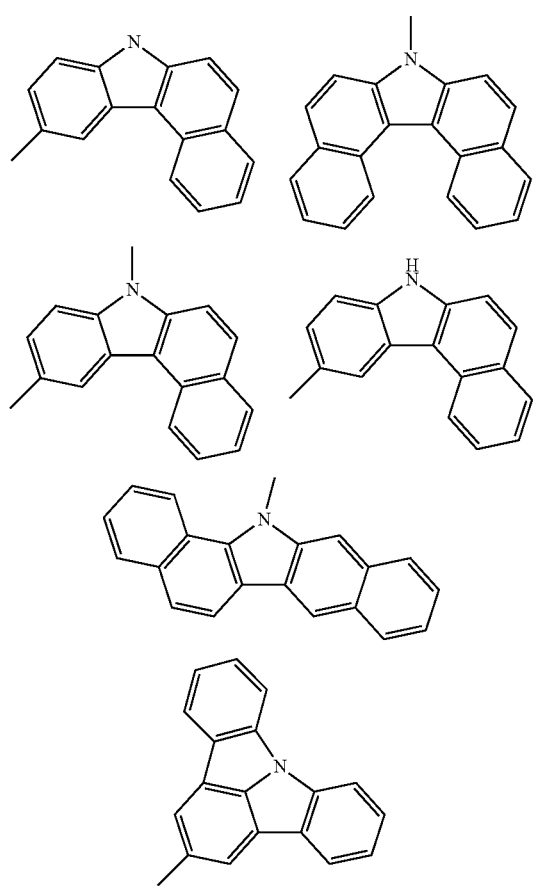
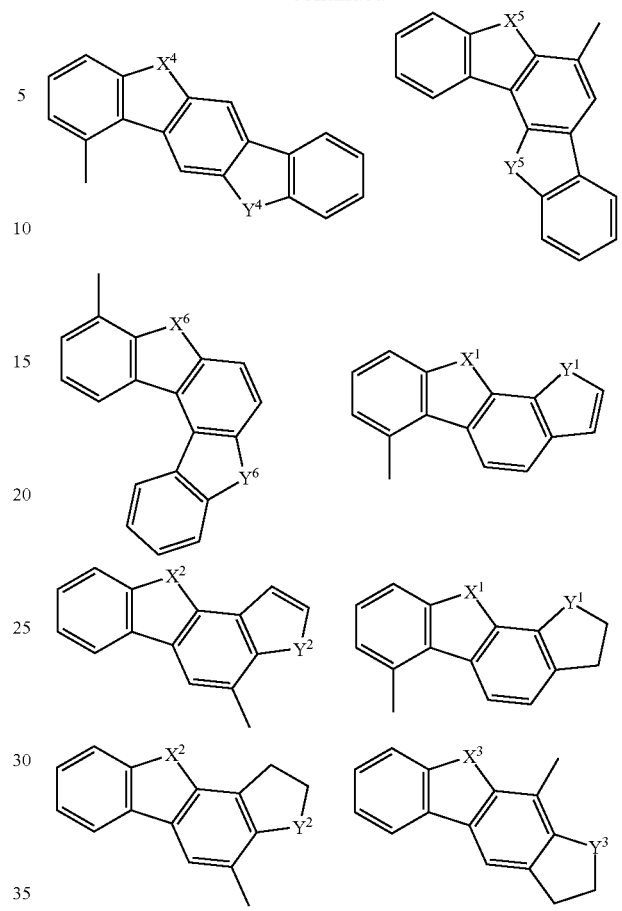
The above-mentioned heteroaryl group also includes the following structures.
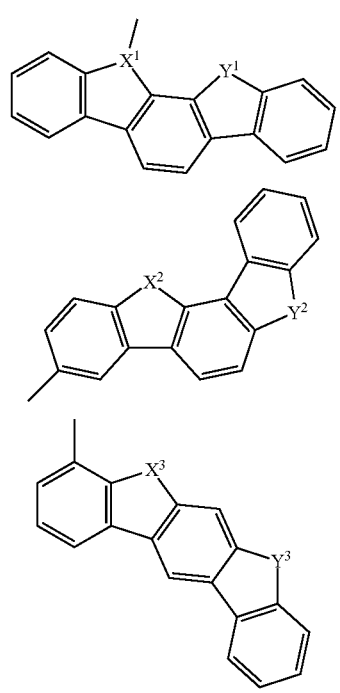
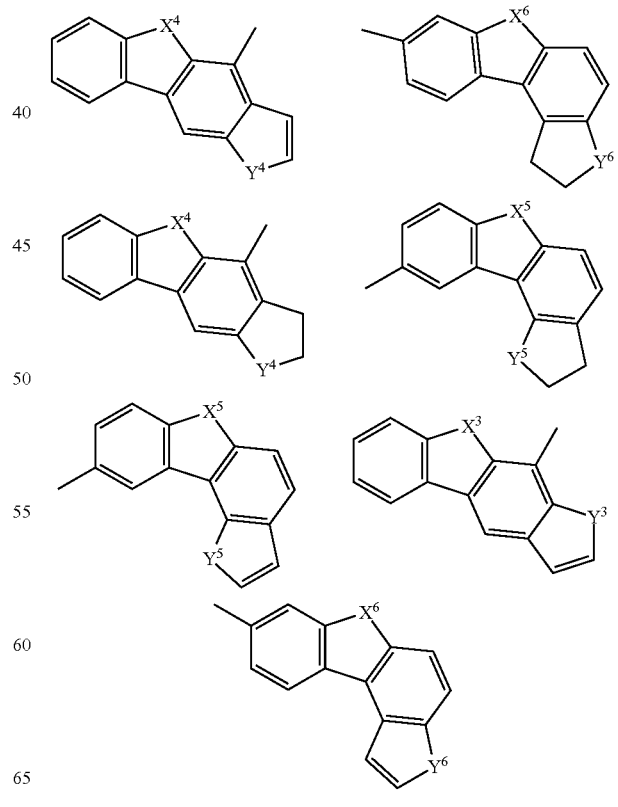

wherein in the formulas, $X^1$ to $X^6$ and $Y^1$ to $Y^6$ are independently an oxygen atom, a sulfur atom, a nitrogen atom or a —NH— group.

As an arbitrary substituent in the "substituent" or the "substituted or unsubstituted", a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, a substituted or unsubstituted heteroaryl group including 5 to 30 ring atoms, —P(=O)$R^{120}R^{121}$ or the like can be given.

$R^{120}$ and $R^{121}$ are independently a substituted or unsubstituted alkyl group including 1 to 25 carbon atoms, a substituted or unsubstituted aryl group including 6 to 30 ring carbon atoms or a substituted or unsubstituted heteroaryl group including 5 to 30 ring atoms.

These substituents may further be substituted by the above-mentioned substituents. In addition, a plurality of these substituents may be bonded with each other to form a ring.

As the halogen atom, fluorine, chlorine, bromine, iodine or the like can be given, with a fluorine atom being preferable.

As the alkyl group, a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group or the like can be given.

The number of carbon atoms of the alkyl group is preferably 1 to 10, with 1 to 6 being further preferable. Among them, a methyl group, an ethyl group, a propyl group, an isopropyl group, a n-butyl group, a s-butyl group, an isobutyl group, a t-butyl group, a n-pentyl group and a n-hexyl group are preferable.

As the cycloalkyl group, a cyclopropyl group, a cyclobutyl group, a cyclopentyl group, a cyclohexyl group, a 4-methylcyclohexyl group, an adamantyl group, a norbornyl group or the like can be given. The number of ring carbon atoms is preferably 3 to 10, with 5 to 8 being further preferable. The number of ring carbon atoms is more preferably 3 to 8, with 3 to 6 being particularly preferable.

The alkylsilyl group is represented by —$SiY_3$. As examples of Y, the examples of alkyl mentioned above can be given. As the alkylsilyl group, a trimethylsilyl group, a triethylsilyl group, a t-butyldimethylsilyl group, a vinyldimethylsilyl group, a propyldimethylsilyl group, a triisopropylsilyl group or the like can be given.

The arylsilyl group is a silyl group substituted by one to three aryl group(s). As examples of the aryl group, the examples of the aryl mentioned above can be given. Other than the aryl group, the arylsilyl group may be substituted by the above-mentioned alkyl group. As the arylsilyl group, a triphenylsilyl group, a phenyldimethylsilyl group or the like can be given.

The alkoxy group is represented by —OY. As examples of Y, the examples of the alkyl mentioned above can be given. The alkoxy group is a methoxy group or an ethoxy group, for example.

The aryloxy group is represented by —OZ. As examples of Z, the examples of the aryl group mentioned above can be given. The aryloxy group is a phenoxy group, for example.

The alkylthio group is represented by —SY. As examples of Y, the examples of the alkyl group mentioned above can be given.

The arylthio group is represented by —SZ. As examples of Z, the examples of the aryl group mentioned above can be given.

The arylamino group is represented by —$NZ_2$. As examples of Z, the example of the aryl group mentioned above can be given.

The aryl group and the heteroaryl group are as mentioned above.

Examples of the compound according to one aspect of the invention will be shown below.

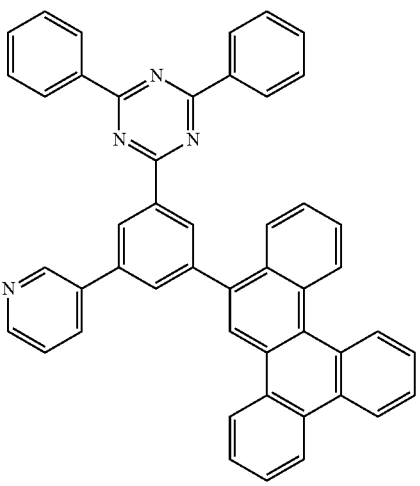

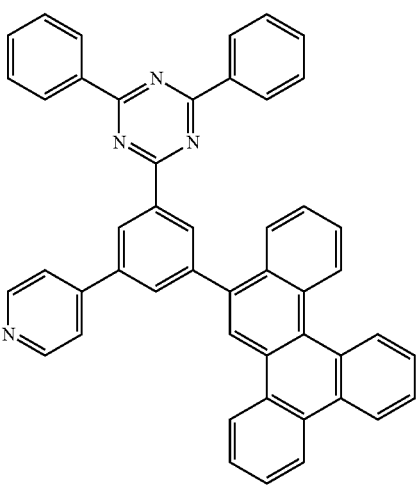

-continued
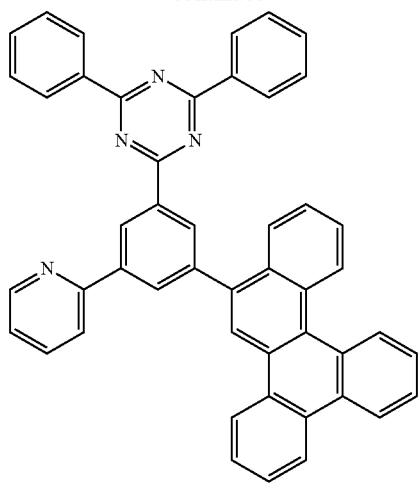
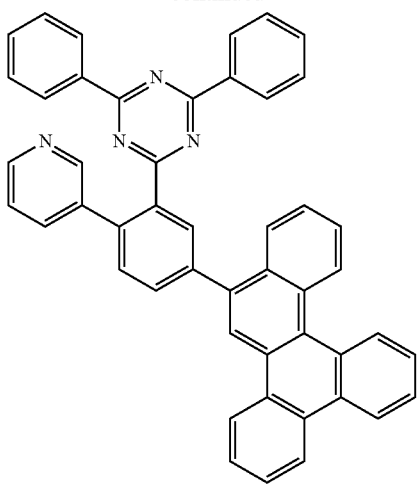
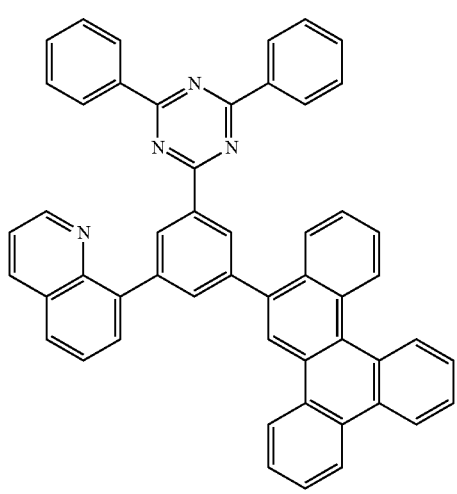
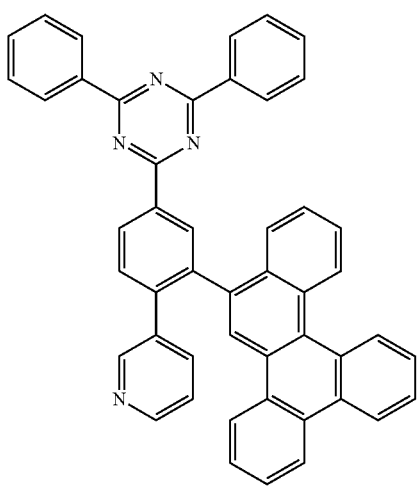
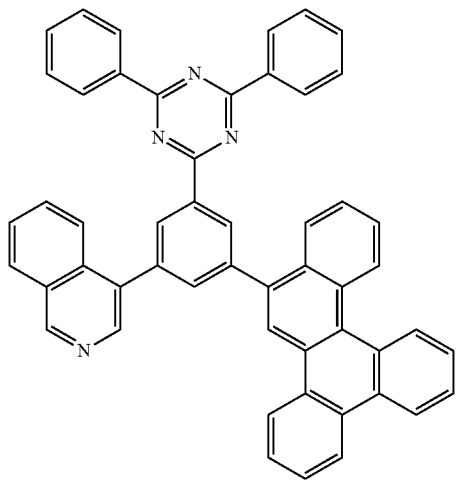
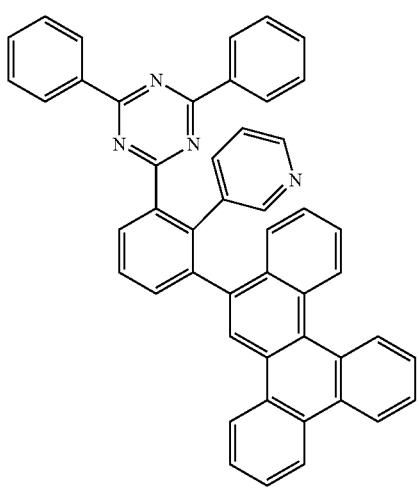

-continued
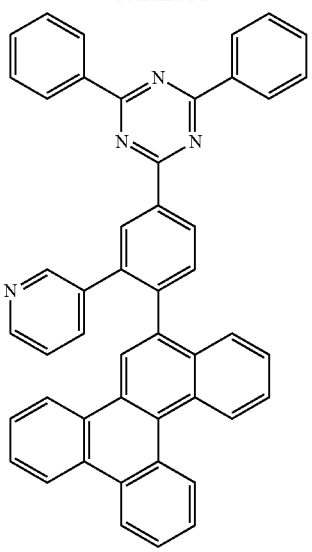
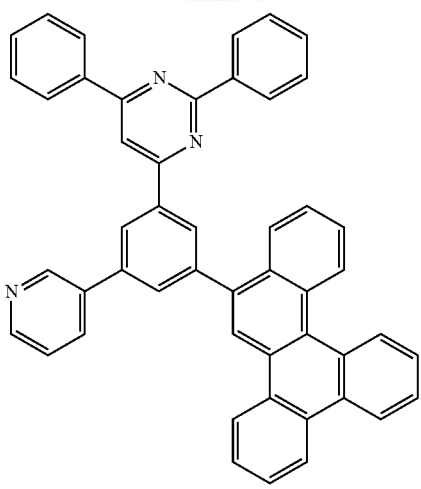
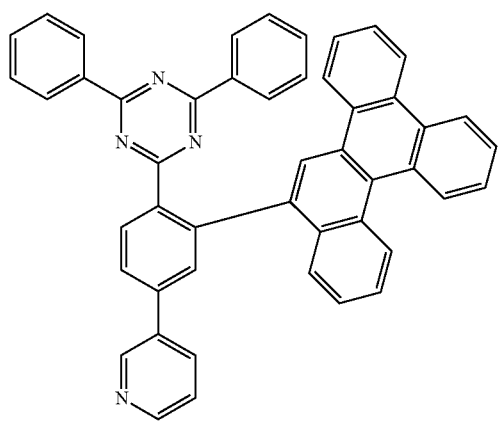
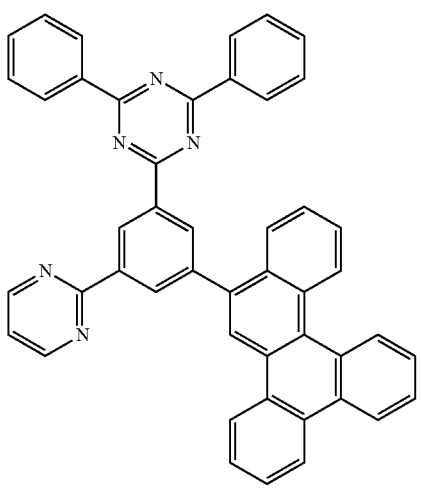
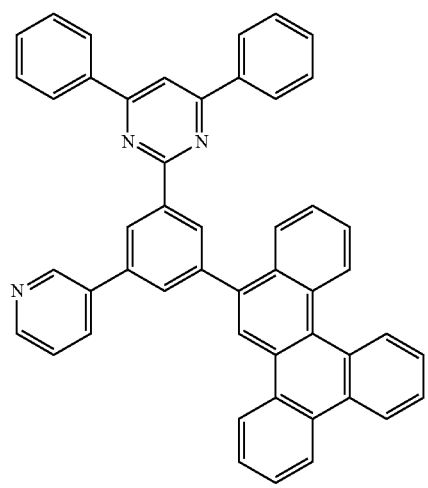
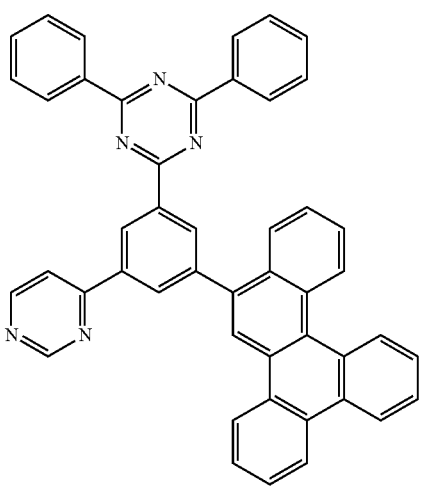

17
-continued
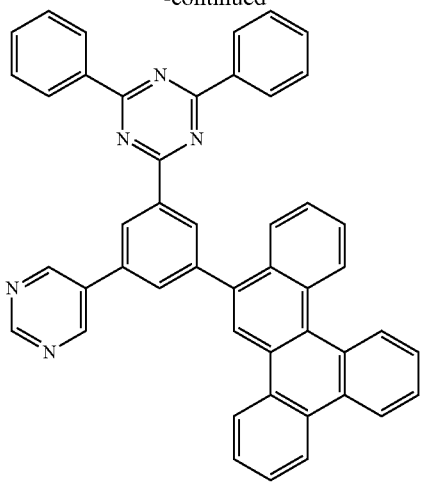
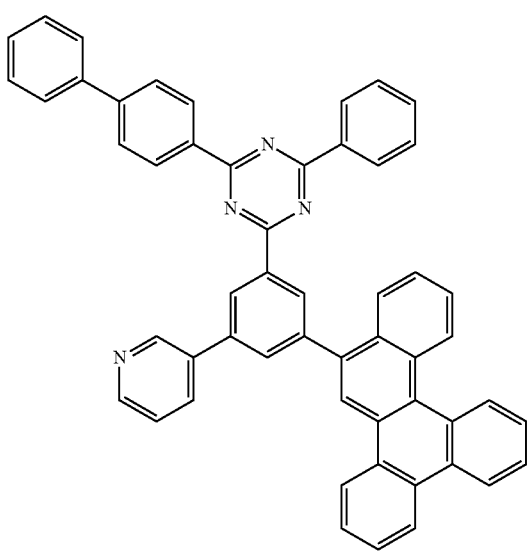
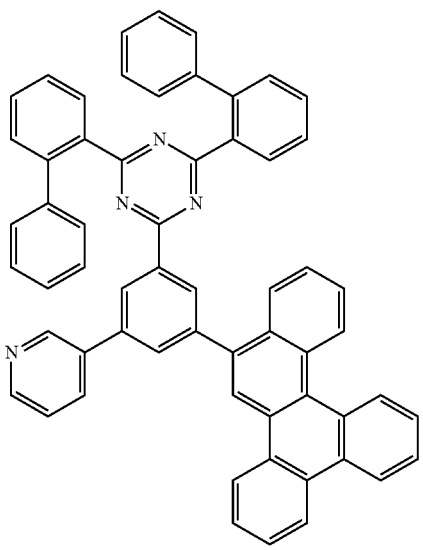
18
-continued
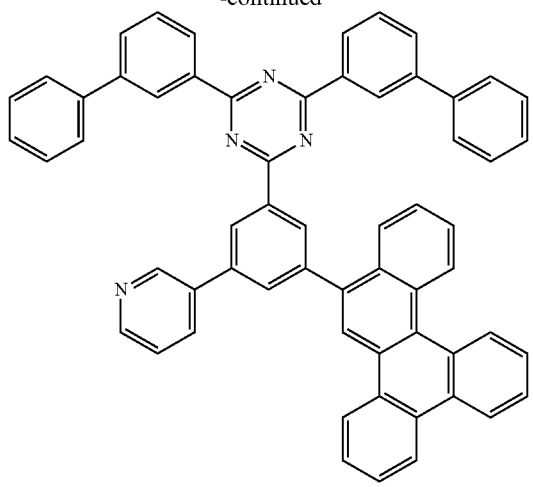
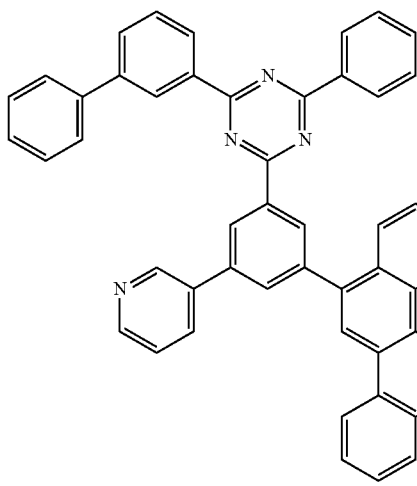

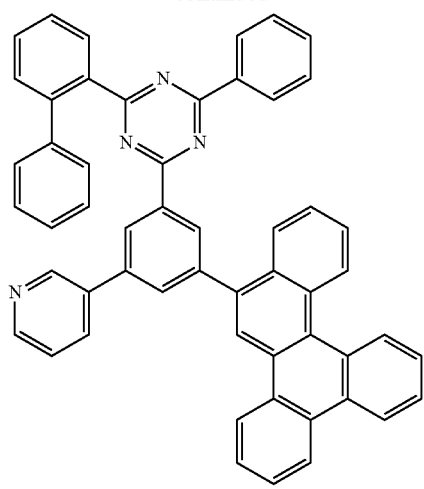
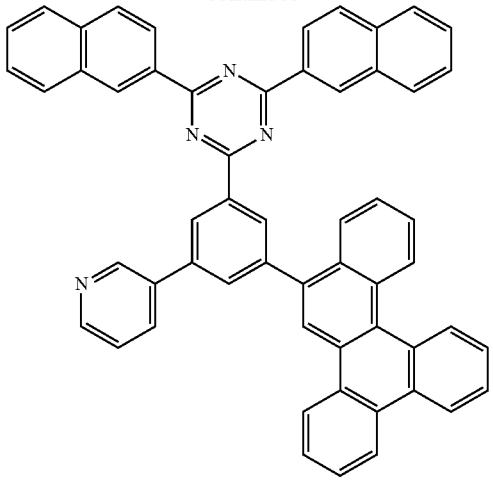
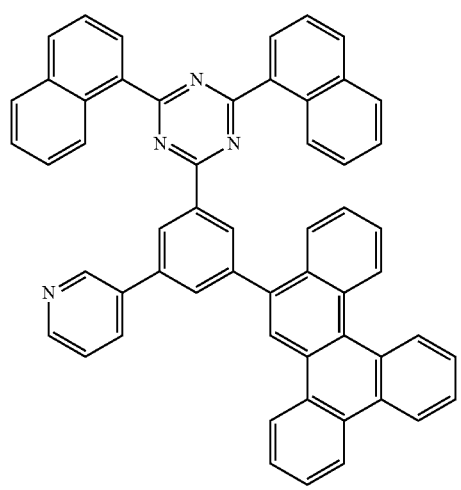
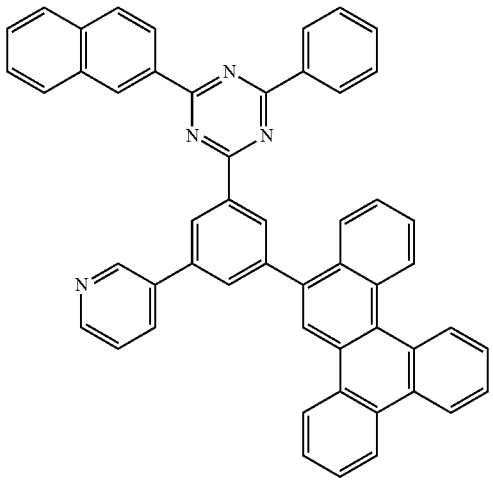
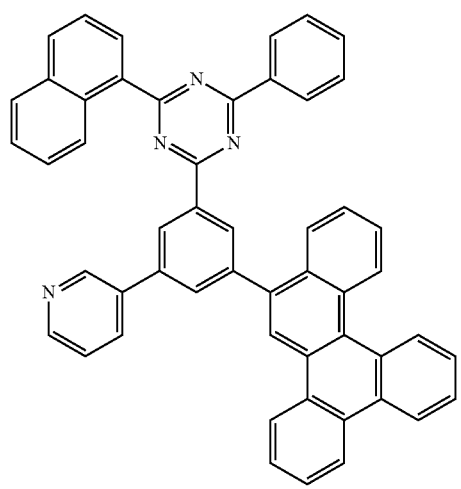
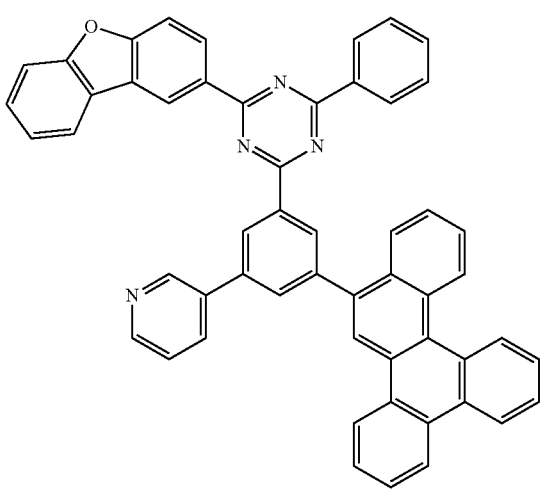

-continued
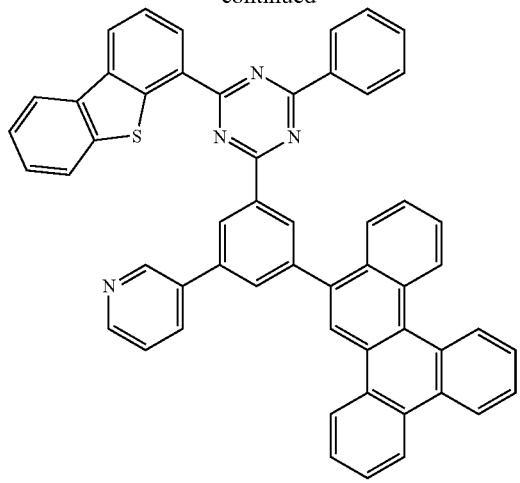
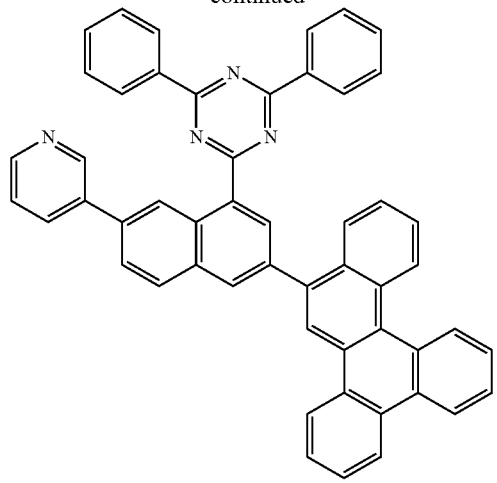
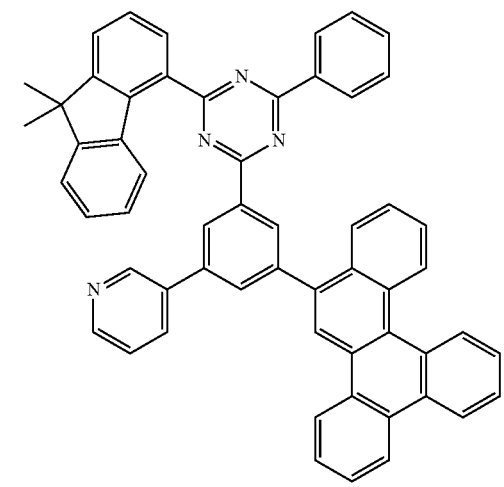
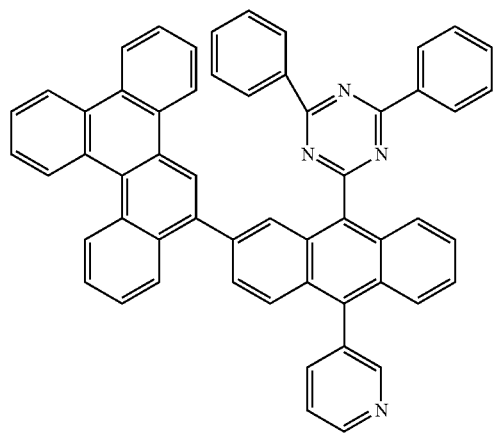
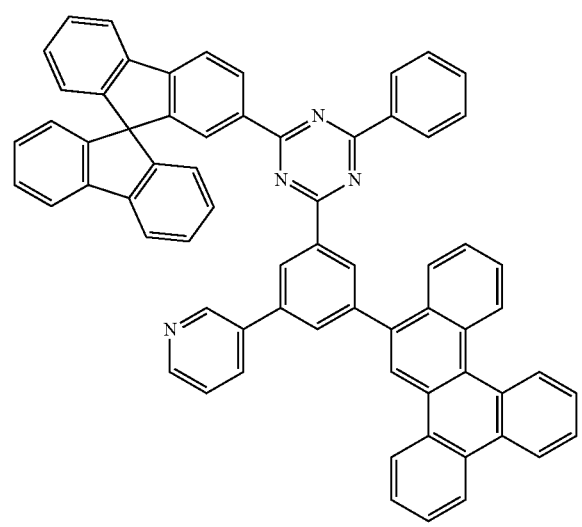
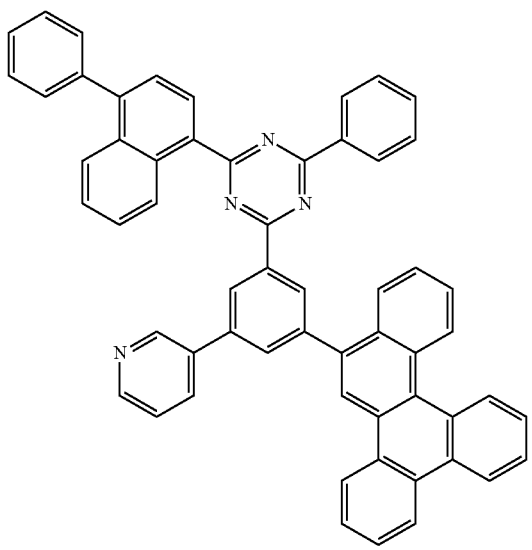

23
-continued
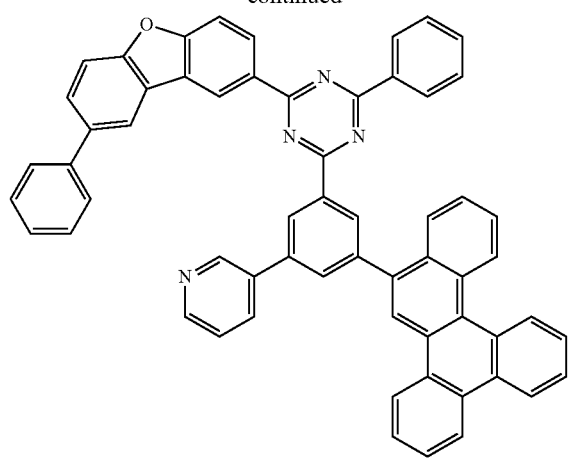
24
-continued
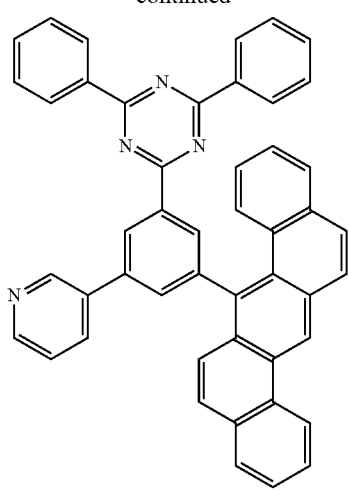
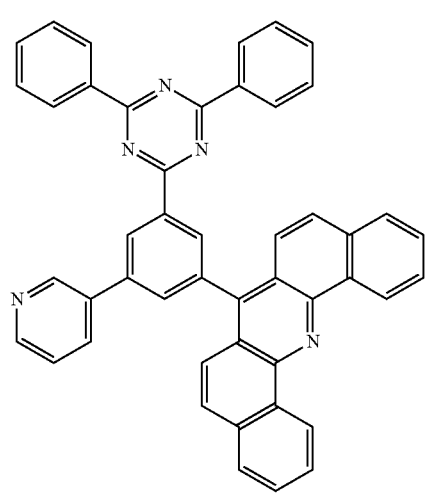
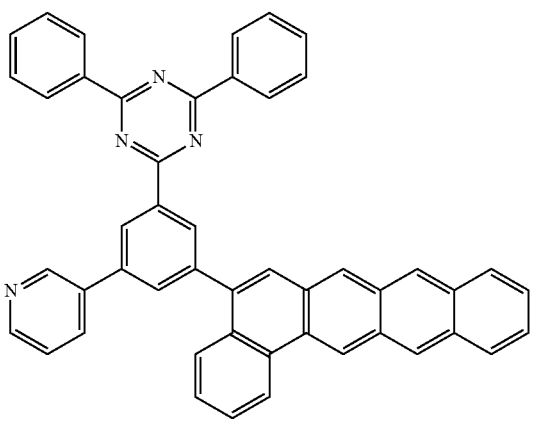
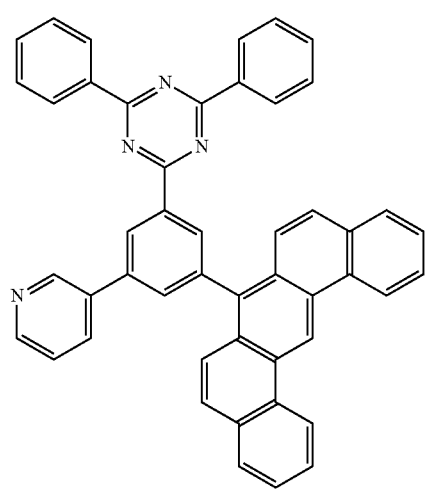
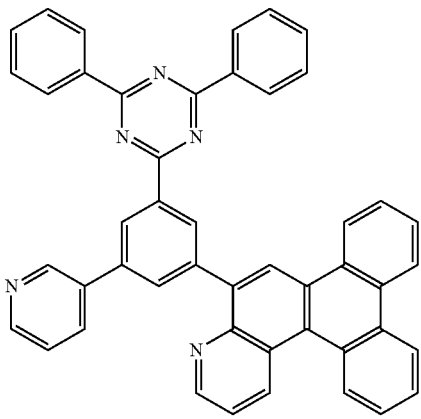

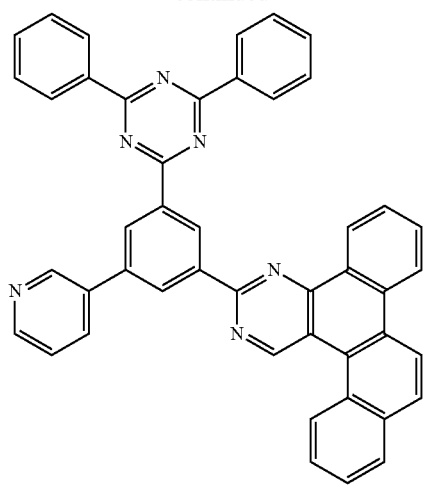
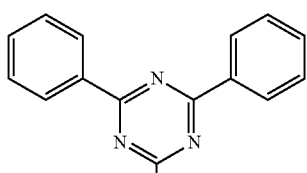
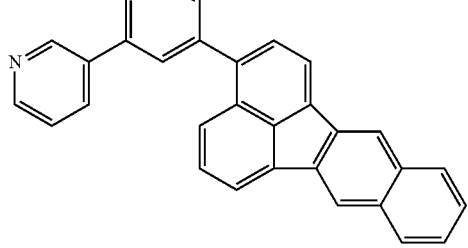
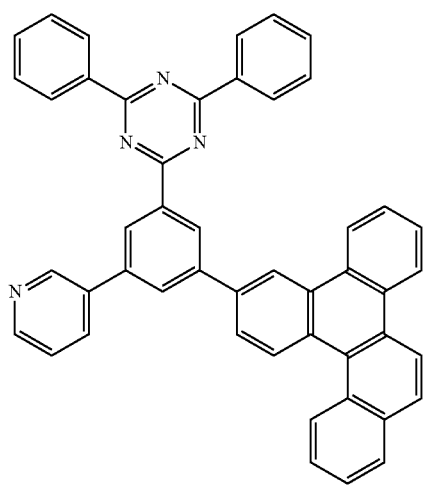
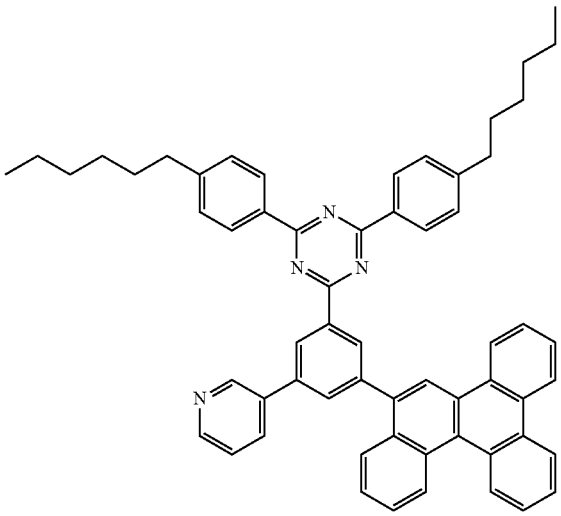
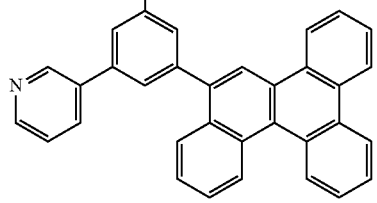
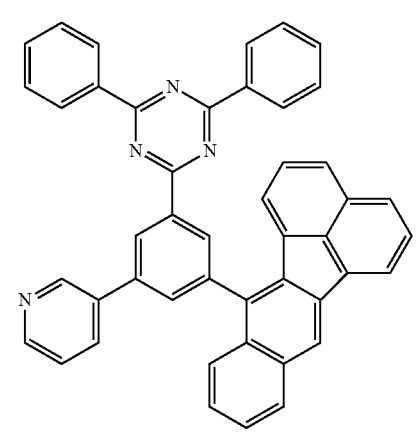
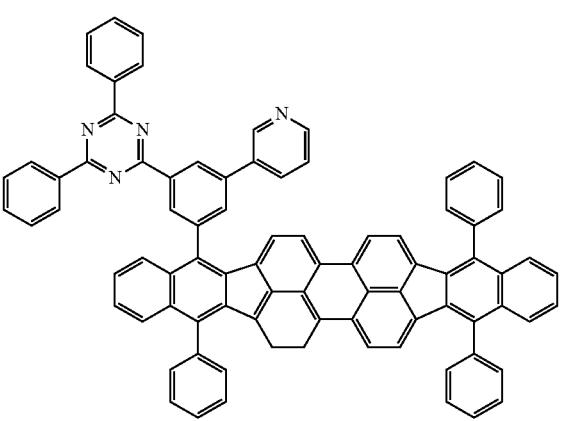

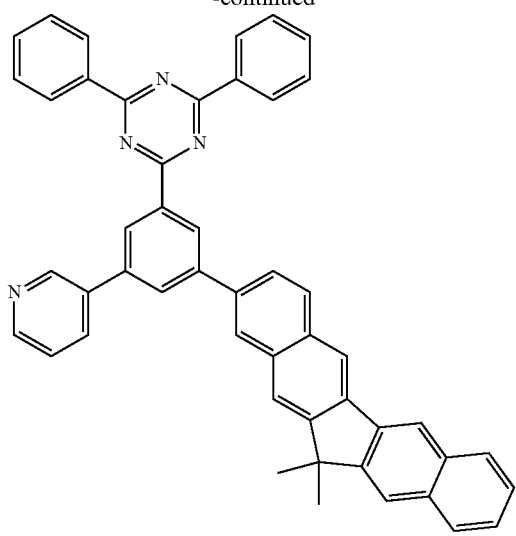
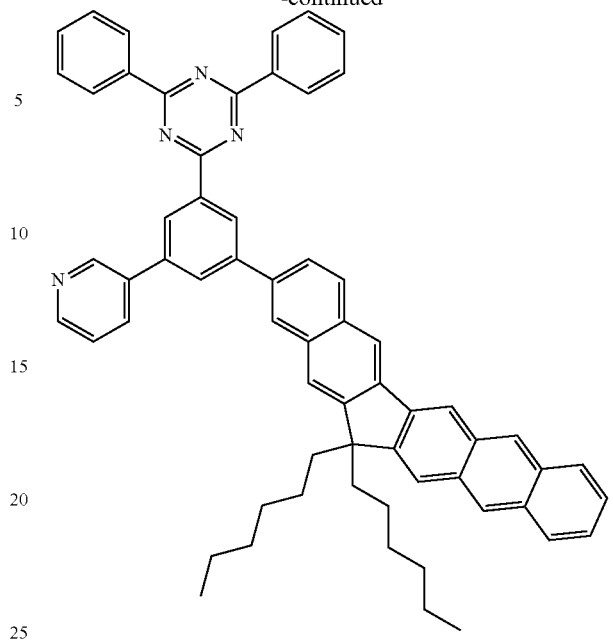
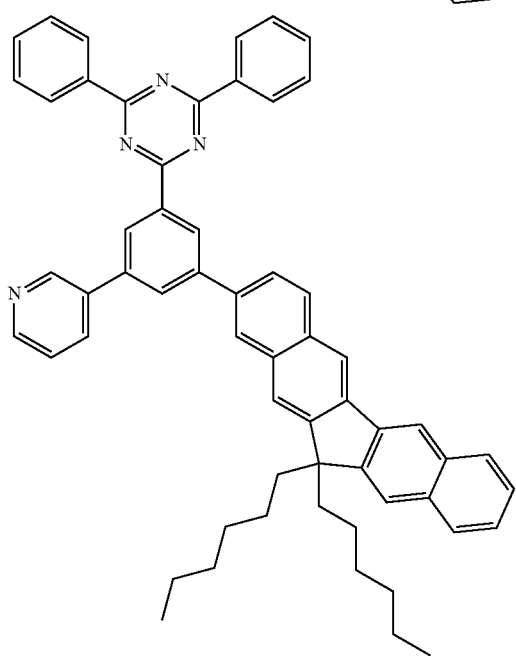
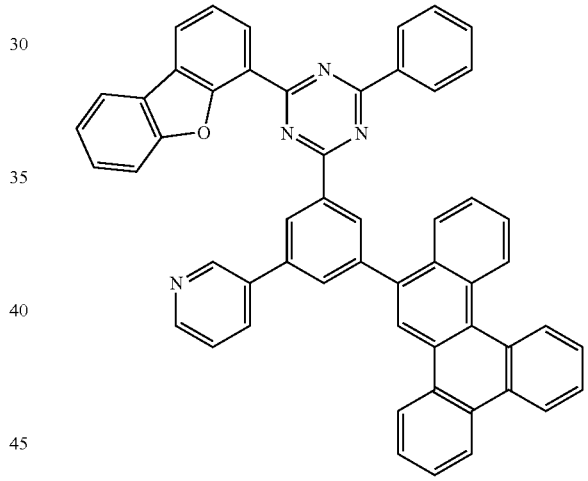
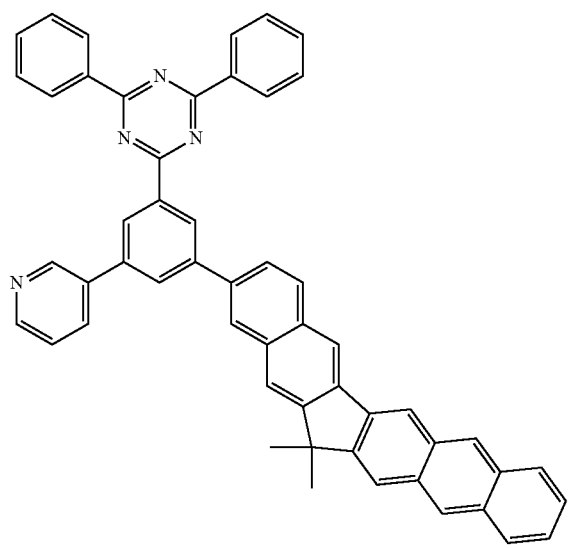
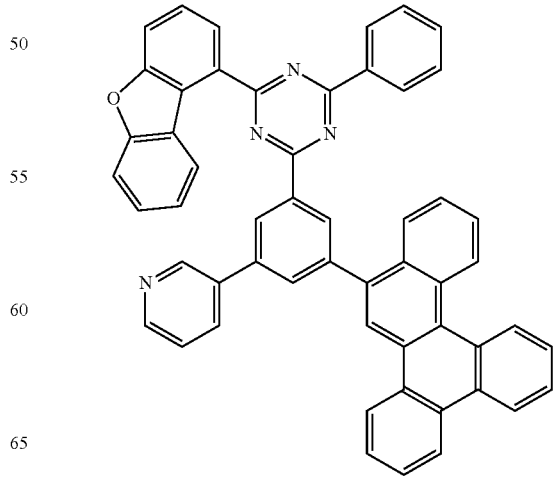

29
-continued
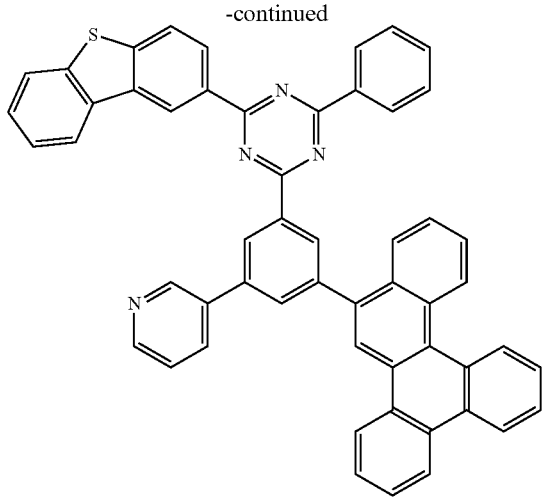
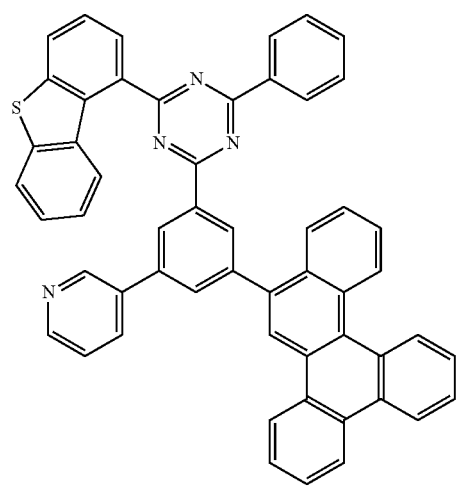
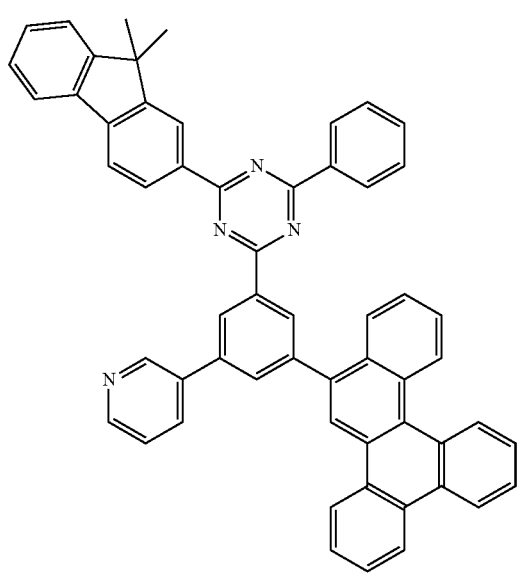
30
-continued
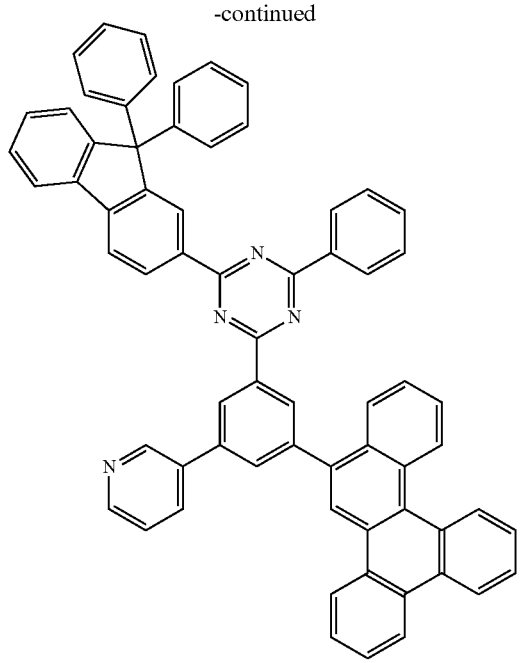
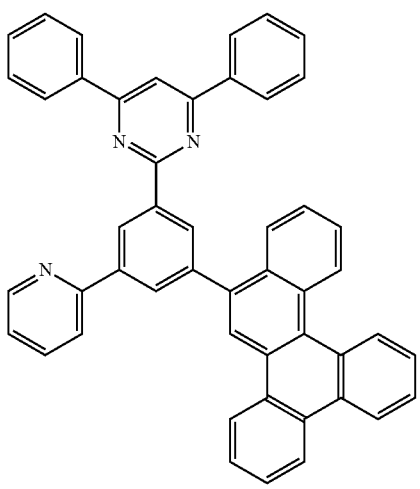
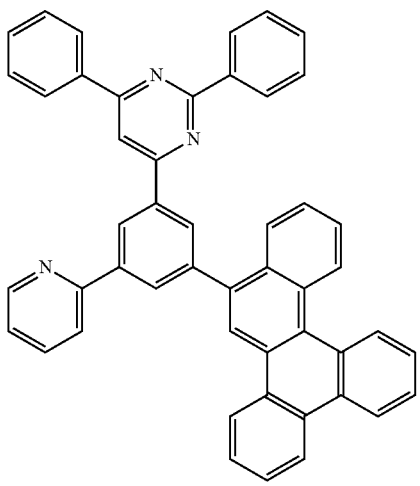

31
-continued
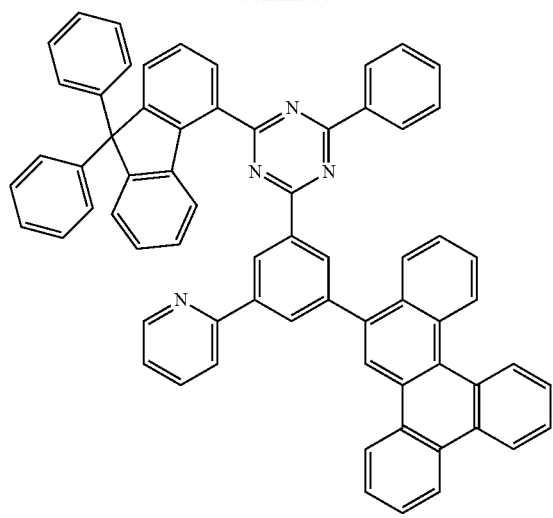
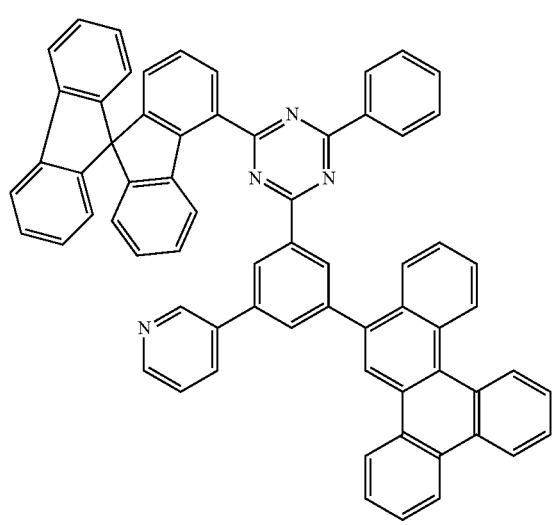
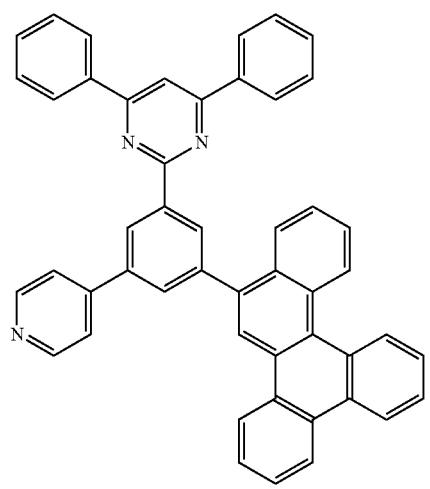
32
-continued
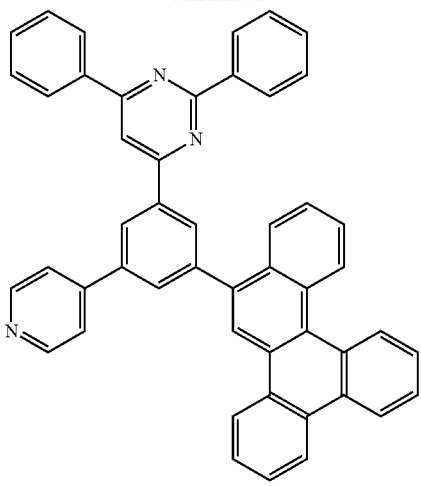
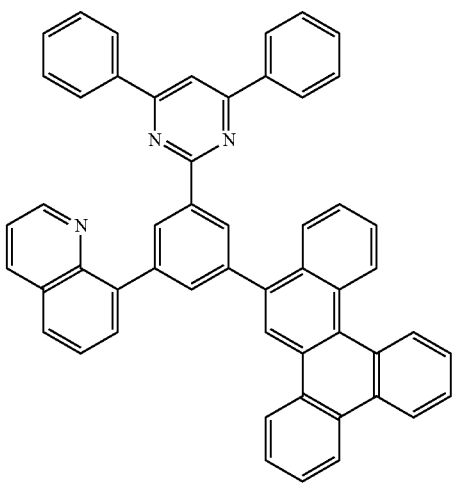
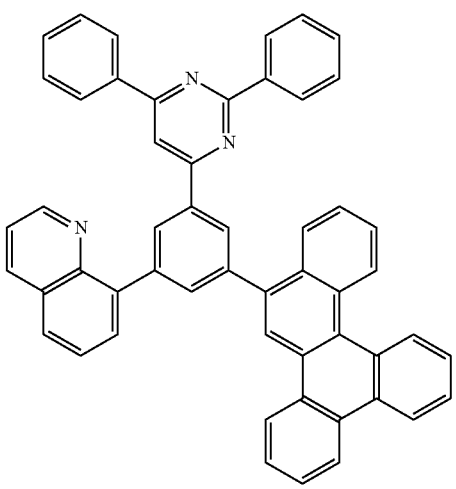 [SMILES: c1ccc(-c2cc(-c3cc(-c4cncc5ccccc45)cc(-c4cc5c6ccccc6c6ccccc6c5c5ccccc45)c3)nc(-c3ccccc3)n2)cc1]

-continued

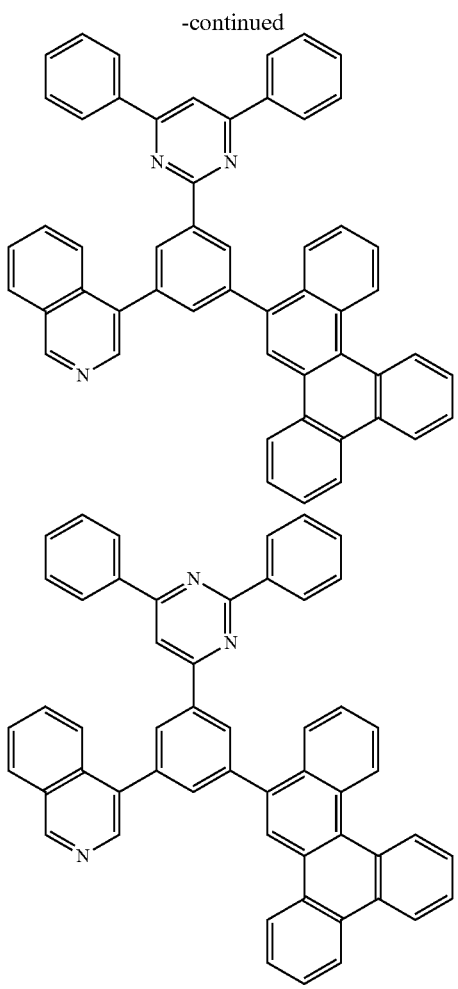

The above-mentioned compound can be used as a material for an organic electroluminescence (EL) device, preferably as an electron-transporting material.

[Organic EL Device]

The organic EL device according to one aspect of the invention has a structure in which it comprises one or more organic thin film layers including an emitting layer between a cathode and an anode, and at least one layer of the organic thin film layers comprises the compound represented by the above formula (1) as a single or mixed component.

The above-mentioned organic EL device preferably has an electron-transporting zone between the emitting layer and the cathode. The electron-transporting zone has one or more organic thin film layers, and at least one layer of the organic thin film layers comprises the compound represented by the formula (1). The at least one layer is preferably an electron-transporting layer.

As the representative device configuration of the organic EL device, a configuration in which the following (1) to (4) or the like are stacked on a substrate can be exemplified.
(1) Anode/Emitting layer/Cathode
(2) Anode/Hole-transporting zone/Emitting layer/Cathode
(3) Anode/Emitting layer/Electron-transporting zone/Cathode
(4) Anode/Hole-transporting zone/Emitting layer/Electron-transporting zone/Cathode
("/" means that the layers are adjacently stacked)

The electron-transporting zone is normally composed of one or more layers selected from the electron-injecting layer and the electron-transporting layer. The hole-transporting zone is normally composed of one or more layers selected from the hole-injecting layer and the hole-transporting layer.

Hereinbelow, each layer of the organic EL device will be explained.

(Substrate)

The substrate is used as a base of an emitting element. As the substrate, glass, quarts, plastic or the like can be used, for example. A flexible substrate may be used. A flexible substrate is a substrate that can be bent. For example, a plastic substrate made of polycarbonate or polyvinyl chloride or the like can be given.

(Anode)

For an anode formed on the substrate, it is preferable to use a metal, an alloy, an electrically conductive compound having a large work function (specifically, 4.0 eV or more), a mixture thereof or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene or the like can be given, for example. In addition, gold (Au), platinum (Pt) or a nitride of a metal material (e.g. titanium nitride) or the like can be given.

(Hole-Injecting Layer)

A hole-injecting layer is a layer that contains a substance having high hole-injection property. As the substance having high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, or a polymer compound (oligomer, dendrimer, polymer, etc.) or the like can be used.

As one preferable aspect of the substance used in the hole-injecting layer, an acceptor compound can be given. As the acceptor compound, a heterocyclic derivative on which an electron-attracting group is substituted, a quinone derivative on which an electron-attracting group is substituted, an arylborane derivative, a heteroarylborane derivative or the like can be preferably used. Among these, hexacyano-hexaazatriphenylene, $F_4TCNQ$ (2,3,5,6-tetrafluoro-7,7,8,8-tetracyanoquinodimethane) or 1,2,3-tris[(cyano)(4-cyano-2,3,5,6-tetrafluorophenyl)methylene]cyclopropane or the like can preferably be used.

A layer that comprises an acceptor compound may further comprise a matrix material. As the matrix material, a wide variety of materials for an organic EL device can be used. As the matrix material used together with the acceptor compound, it is preferable to use a donor compound. It is further preferable to use an aromatic amine compound.

(Hole-Transporting Layer)

A hole-transporting layer is a layer that contains a substance having high hole-transporting property. In the hole-transporting layer, aromatic amine compounds, carbazole derivatives, anthracene derivatives and the like can be used. Polymer compounds such as poly(N-vinylcarbazole) (abbreviation: PVK) or poly(4-vinyltriphenylamine) (abbreviation: PVTPA) can also be used. As long as it has high hole-transporting property rather than electron-transporting property, other substances than those mentioned above can be used. The layer containing the substance having high hole-transporting property may be not only a single layer but also a layer obtained by stacking two or more layers containing the above-mentioned substances.

The hole-transporting material is preferably a compound represented by the following general formula (H):

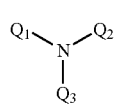

(H)

In the general formula (H), $Q_1$ to $Q_3$ are independently a substituted or unsubstituted aromatic hydrocarbon group including 6 to 50 ring carbon atoms, a substituted or unsubstituted aromatic heterocyclic group including 5 to 50 ring atoms or a group composed of a combination of a substituted or unsubstituted aromatic hydrocarbon group and a substituted or unsubstituted heterocyclic group.

As the aromatic hydrocarbon group, substituents such as a phenyl group, a biphenyl group, a terphenyl group, a fluorenyl group, a spirobifluorenyl group, an indenofluorenyl group, a naphthyl group, a phenanthryl group, an anthryl group, a triphenylenyl group and the like are preferable. As the aromatic heterocyclic group, a dibenzofuranyl group, a dibenzothiophenyl group, a carbazolyl group or the like are preferable. As the group composed of a combination of the aromatic hydrocarbon group and the aromatic heterocyclic group, a dibenzofuran-substituted aromatic hydrocarbon group, a dibenzothiophene-substituted aromatic hydrocarbon group, a carbazole-substituted aromatic hydrocarbon group and the like are preferable. These substituents may further have a substituent.

As one preferable aspect, it is preferred that at least one of $Q_1$ to $Q_3$ in the general formula (H) be a compound that is further substituted by an arylamino group. It is also preferred that at least one of $Q_1$ to $Q_3$ be a diamine derivative, a triamine derivative or a tetraamine derivative. As the diamine derivative, tetraaryl-substituted benzidine derivatives and TPTE (4,4'-bis[N-phenyl-N-[4'-diphenylamino-1,1'-biphenyl-4-yl]amino]-1,1'-biphenyl] and the like are preferable used.

(Guest Material of Emitting Layer)

An emitting layer is a layer that contains a substance having high emitting property, and various materials can be used for the emitting layer. For example, as the substance having high emitting property, a fluorescent compound that emits fluorescence or a phosphorescent compound that emits phosphorescence can be used. A fluorescent compound is a compound that can emit light from the singlet excited state, and a phosphorescent compound is a compound that can emit light from the triplet excited state.

As the blue fluorescent emitting material that can be used in the emitting layer, pyrene derivatives, styrylamine derivatives, chrysene derivatives, fluoranthene derivatives, fluorene derivatives, diamine derivatives, triarylamine derivatives and the like can be given. As the green fluorescent emitting material that can be used in the emitting layer, an aromatic amine derivative and the like can be used. As the red fluorescent emitting material that can be used in the emitting layer, tetracene derivatives, diamine derivatives and the like can be given.

As the fluorescent emitting material that can be used in the emitting layer, among others, a fused polycyclic aromatic derivative, a styrylamine derivative, a fused-ring amine derivative, a boron-containing compound, a pyrrole derivative, an indole derivative, a carbazole derivative and the like are preferable. As the fluorescent emitting material that can be used in the emitting layer, further preferably, a fused-ring amine derivative and a boron-containing compound can be given. A fused ring amine derivative is preferably a compound represented by the following general formula (J):

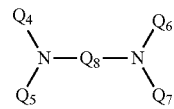

(J)

In the general formula (J), $Q_4$ to $Q_7$ are independently a substituted or unsubstituted aromatic hydrocarbon group including 6 to 50 ring carbon atoms or a substituted or unsubstituted aromatic heterocyclic group including 5 to 50 ring atoms.

As the above-mentioned aromatic hydrocarbon group including 6 to 50 ring carbon atoms, an aromatic hydrocarbon group including 6 to 12 ring carbon atoms is further preferable, with a phenyl group being particularly preferable. As the aromatic heterocyclic group including 5 to 50 ring atoms, a carbazolyl group, a dibenzofuranyl group, a dibenzothiophenyl group and the like can be given, with a dibenzofuranyl group being preferable.

$Q_8$ is a substituted or unsubstituted divalent aromatic hydrocarbon group including 6 to 50 ring carbon atoms or a substituted or unsubstituted divalent aromatic hydrocarbon group including 5 to 50 ring atoms.

As the divalent aromatic hydrocarbon group including 6 to 50 ring carbon atoms, a pyrenyl group, a chrysenyl group, an anthracenyl group, a fluorenyl group or the like can be given, with a pyrenyl group being preferable. As the divalent aromatic hydrocarbon group including 6 to 50 ring carbon atoms, a fluorenyl group to which one or more benzofuro skeleton(s) is (are) fused is preferable.

Examples of the boron-containing compound include a pyrromethene derivative and a triphenylborane derivative. The "derivative" as used herein refers to a compound containing said skeleton as a partial structure thereof, and includes a compound further forming a fused ring and a compound forming a ring by substituents. For example, in the case of a fused polycyclic aromatic derivative, it is a compound containing a fused polycyclic aromatic skeleton as a partial structure thereof, and a compound that further forms a fused ring in the fused polycyclic aromatic skeleton, and a compound that forms a ring by substituents of the fused polycyclic aromatic skeleton.

As the blue phosphorescent emitting material that can be used in the emitting layer, a metal complex such as an iridium complex, an osmium complex and a platinum complex can be given. As the green phosphorescent emitting material that can be used in the emitting layer, an iridium complex and the like can be given. As the red phosphorescent emitting material, a metal complex such as an iridium complex, a platinum complex, a terbium complex and a europium complex can be given.

The phosphorescent emitting material that can be used in the emitting layer, and that is an ortho-metallated complex of a metal element selected from iridium, osmium and platinum, is preferably a complex represented by the following formula (K).

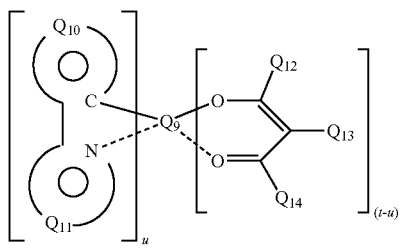

(K)

In the general formula (K), $Q_9$ is at least one metal selected from the group consisting of osmium, iridium and platinum, t is the valence of the metal, and u is 1 or more.

The ring $Q_{10}$ is a substituted or unsubstituted aromatic hydrocarbon group including 6 to 24 ring carbon atoms or an aromatic heterocyclic group including 5 to 30 ring atoms and the ring $Q_{11}$ is a substituted or unsubstituted aromatic heterocyclic group including 5 to 30 ring atoms that includes a nitrogen atom as an atomic element constituting the heterocycle. $Q_{12}$ to $Q_{14}$ are independently a hydrogen atom or a substituent.

When u is 2 or more, plural rings $Q_{10}$ and plural rings $Q_{11}$ may be independently the same as or different from each other.

When (t-u) is 2 or more, plural $Q_{12}$ to $Q_{14}$ may independently be the same as or different from each other.

When (t-u) is zero, the general formula (K) is represented by the following general formula (G), and $Q_9$, ring $Q_{10}$, ring $Q_{11}$ and t are as defined in the general formula (K).

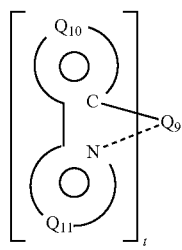

(G)

(Host Material of Emitting Layer)

The emitting layer may have a structure in which the above-mentioned substance having high emitting property (guest material) is dispersed in other substances (host material). As the substance for dispersing the substance having high emitting property, various substances can be used. It is preferable to use a substance having a higher lowest unoccupied molecular orbital (LUMO level) than that of the substance having high emitting property, and having a lower highest unoccupied molecular orbital (HOMO level) than that of the substance having high emitting property.

As the substance for dispersing a substance having high emitting property (host material), 1) a metal complex such as an aluminum complex, a beryllium complex, a zinc complex or the like, 2) a heterocyclic compound such as an oxadiazole derivative, a benzimidazole derivative, a phenanthroline derivative and the like, 3) a fused aromatic compound such as a carbazole derivative, an anthracene derivative, a phenanthrene derivative, a pyrene derivative, a chrysene derivative and the like and 4) an aromatic amine compound such as a triarylamine derivative, a fused polycyclic aromatic amine derivative and the like can be given.

As the host material of the fluorescent emitting layer, among others, a compound having a fused polycyclic aromatic derivative as its main skeleton is preferable, with an anthracene derivative, a pyrene derivative, a chrysene derivative, a naphthacene derivative and the like can be given. A host that is particularly preferable as a blue host material (a host material that can be used with a blue fluorescent emitting material) and a green host material (a host material that can be used with a green fluorescent emitting material) is an anthracene derivative that is represented by the following formula (E).

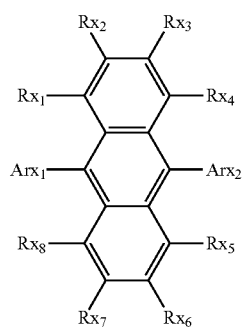

(E)

In the general formula (E), $Ar_{x1}$ and $Ar_{x2}$ are independently a substituted or unsubstituted aromatic hydrocarbon group including 6 to 50 ring carbon atoms or a substituted or unsubstituted aromatic heterocyclic group including 5 to 50 ring atoms. Preferably, $Ar_{x1}$ and $Ar_{x2}$ are independently a substituted or unsubstituted aromatic hydrocarbon group including 6 to 30 ring carbon atoms or a substituted or unsubstituted aromatic heterocyclic group including 5 to 30 ring atoms. Further preferably, $Ar_{x1}$ and $Ar_{x2}$ are independently a substituted or unsubstituted phenyl group, a substituted or unsubstituted naphthyl group, a substituted or unsubstituted biphenyl group, a substituted or unsubstituted phenanthryl group, a substituted or unsubstituted fluorenyl group, a substituted or unsubstituted dibenzofuranyl group, a substituted or unsubstituted naphthobenzofuranyl group or a substituted or unsubstituted carbazolyl group. $R_{x1}$ to $R_{x8}$ are independently a hydrogen atom or a substituent.

As the host material of the phosphorescent emitting material, a carbazole derivative, a carbazole derivative substituted with carbazole, a carbazole derivative to which a benzo skeleton is fused to form a ring, a carbazole derivative to which an indeno skeleton is fused to form a ring, a carbazole derivative to which an indolo skeleton is fused to form a ring, a carbazole derivative to which a benzofuro skeleton is fused to form a ring, a triazine derivative, a pyrimidine derivative, a quinazoline derivative, a fluoranthene derivative, a triphenylene derivatives are preferable.

(Electron-Transporting Layer)

An electron-transporting layer is a layer containing a substance having high electron-transporting property. In the electron-transporting layer, 1) a metal complex such as an aluminum complex, a beryllium complex or a zinc complex, 2) a heteroaromatic compound such as an imidazole derivative, a benzimidazole derivative, an azine derivative, a carbazole derivative or a phenanthroline derivative, and 3) a polymer compound can be used.

Materials to be used for the electron-transporting layer are preferably imidazole derivatives (benzimidazole derivatives, imidazopyridine derivatives, and benzimidazophenanthridine derivatives, for example), azine derivatives (pyrimidine derivatives, triazine derivatives, quinoline derivatives, isoquinoline derivatives, and phenanthroline derivatives, for example, and the heterocyclic ring thereof may be substituted with phosphine oxide-based substituents), and aromatic hydrocarbon derivatives (for example, anthracene derivatives and fluoranthene derivatives can be given). In one preferred form, the electron-transporting zone comprises two or more electron-transporting layers, and one of the electron-transporting layers comprises the compound according to one embodiment of the invention, and the other of the electron-transporting layers comprises the above-mentioned materials for the electron-transporting layer. In another preferred form, one electron-transporting layer comprises both the compound according to one embodiment of the present invention and the above-mentioned materials for the electron-transporting layer. Specific examples of the materials used for the electron-transporting layer are shown below, but the materials are not limited thereto.

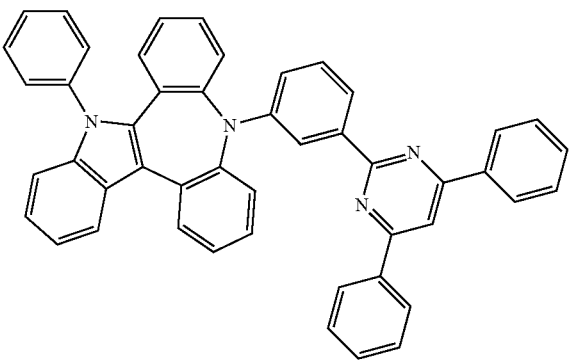

-continued

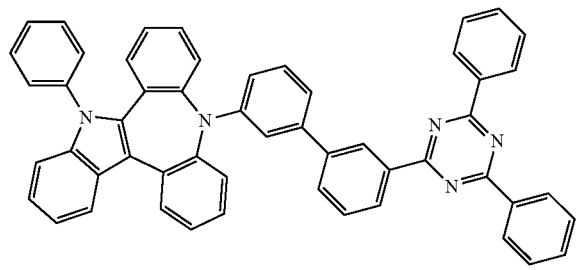

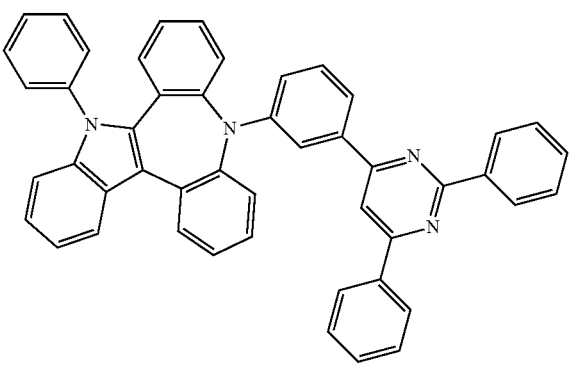

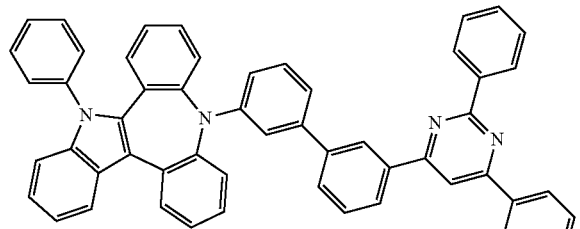

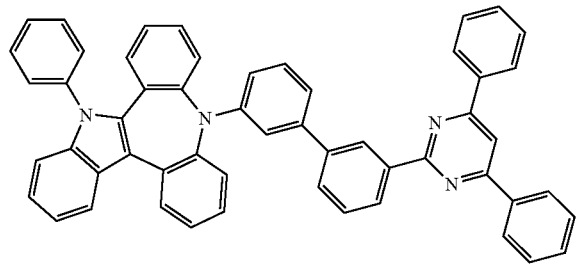

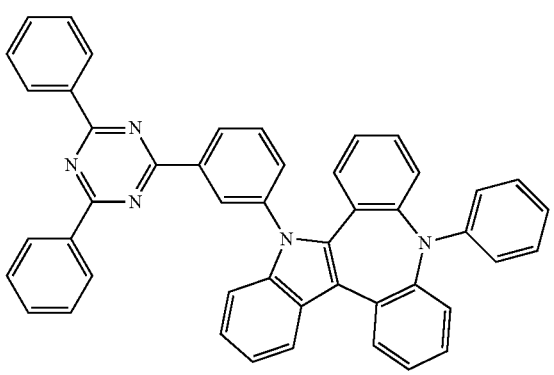

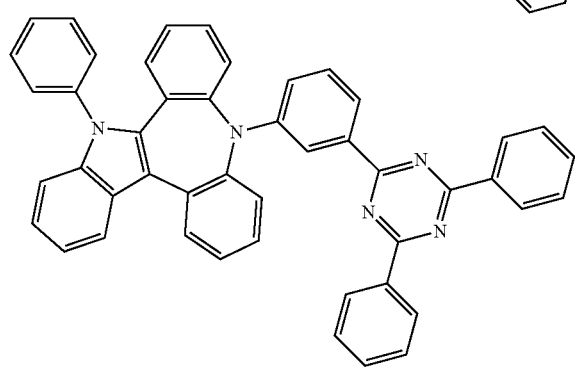

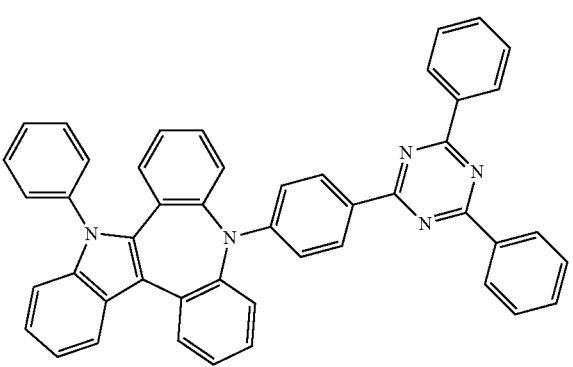

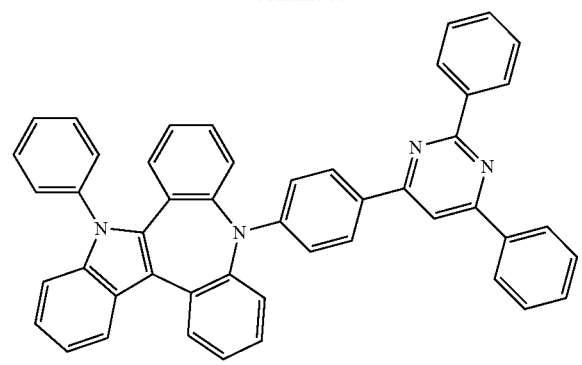
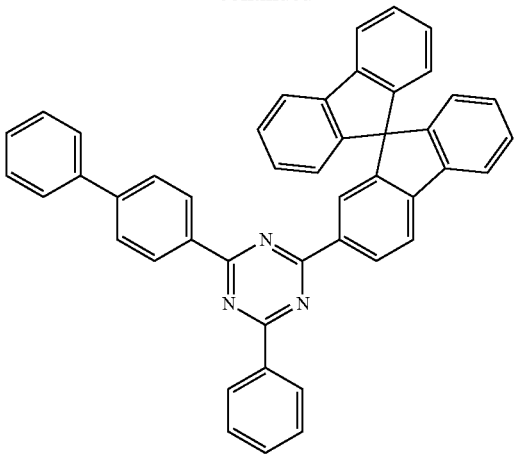
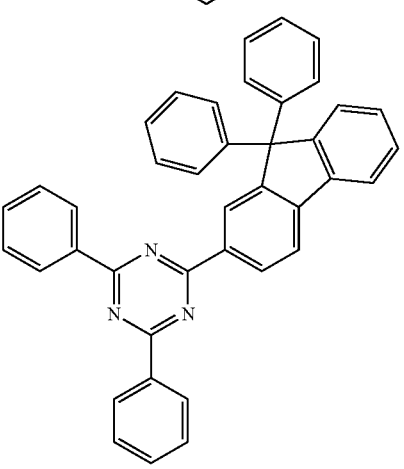
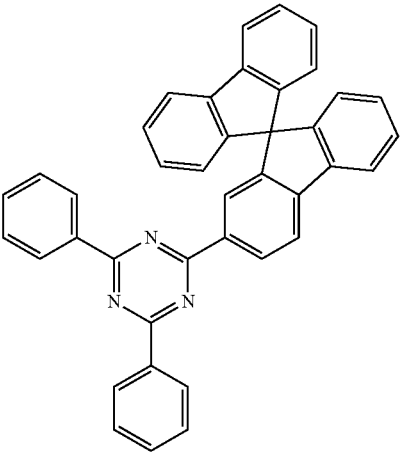
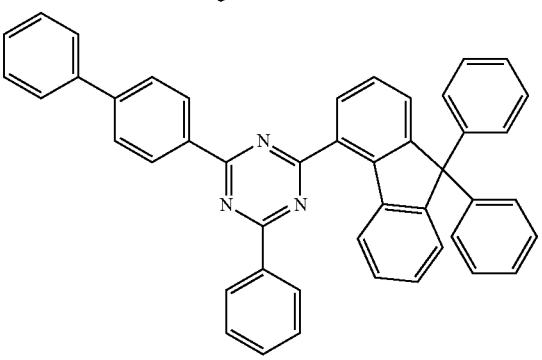

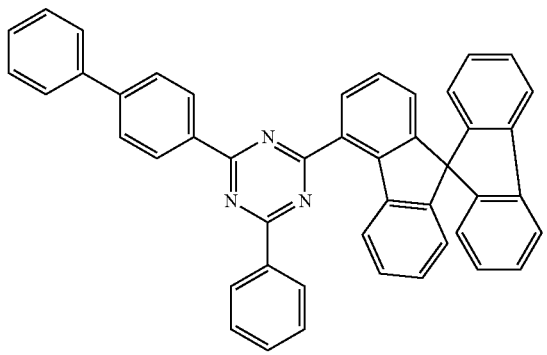
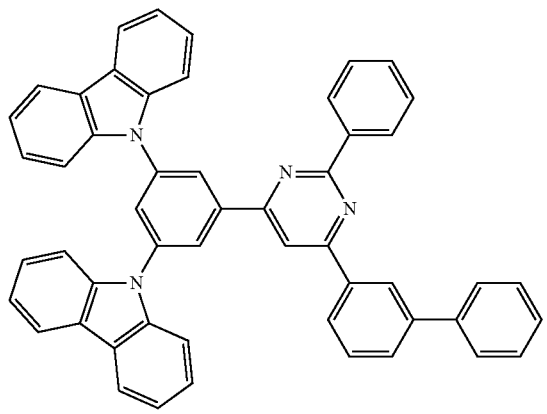
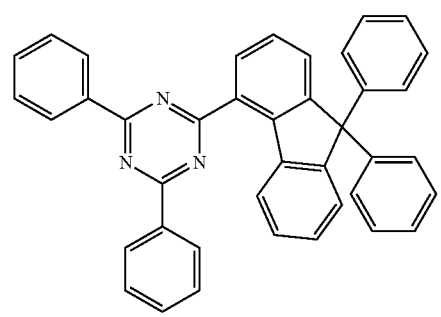
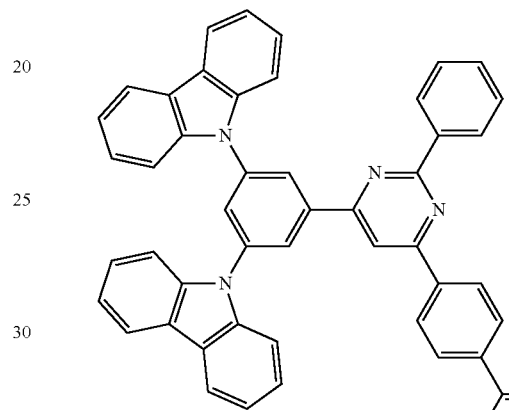
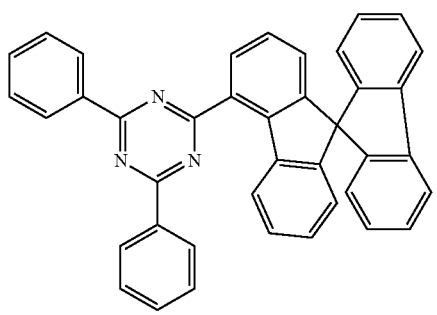
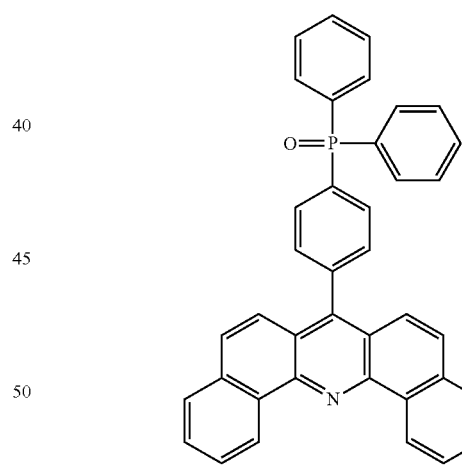
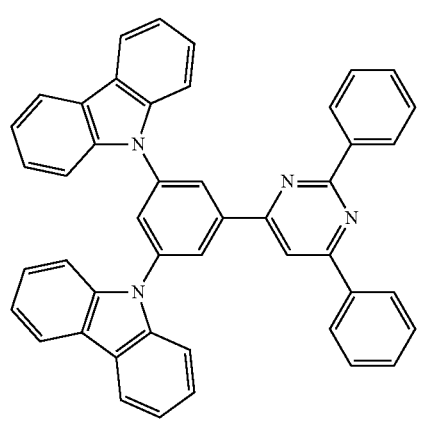
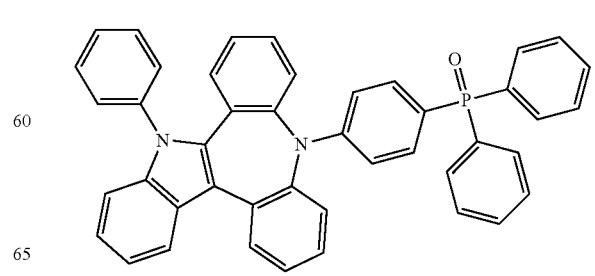

-continued

-continued

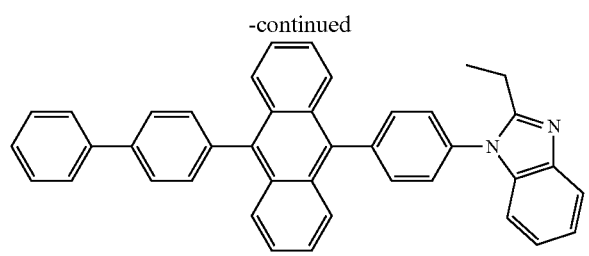

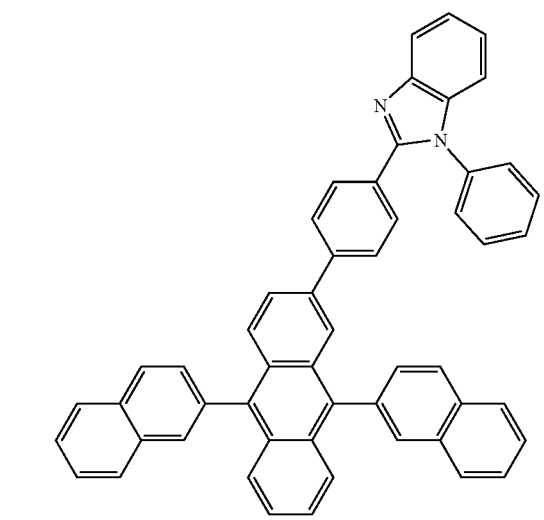

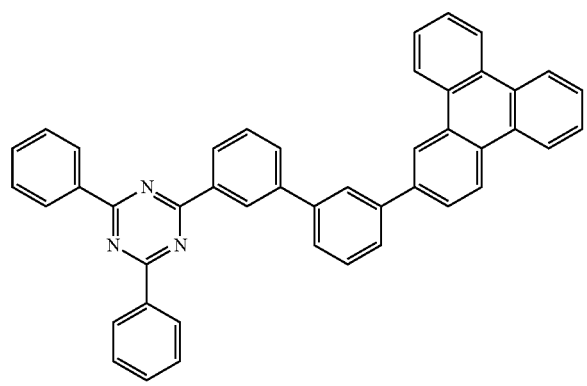

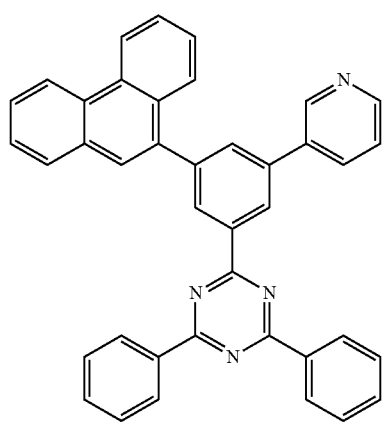

-continued

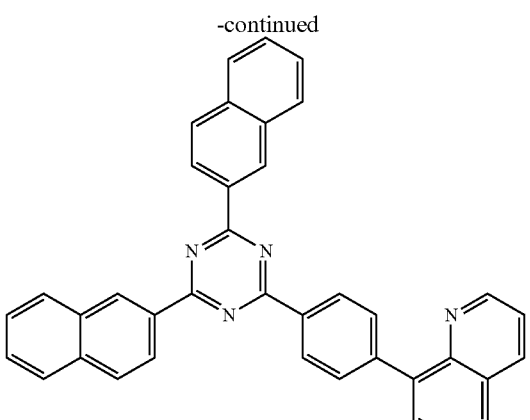

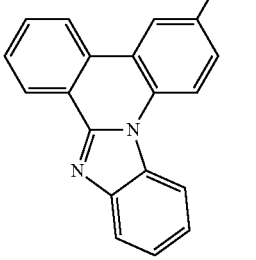

(Electron-Injecting Layer)

An electron-injecting layer is a layer containing a substance having high electron injection property. In the electron-injecting layer, an alkali metal, an alkaline earth metal or a compound of those such as lithium (Li), lithium fluoride (LiF), cesium fluoride (CsF), calcium fluoride ($CaF_2$) and lithium oxide ($LiO_x$) can be used.

It is preferred that the electron-transporting zone further comprise one or more selected from an electron-donating dopant and an organic metal complex.

As the electron-donating dopant, at least one selected from an alkali metal, an alkali metal compound, an alkaline earth metal, an alkaline earth metal compound, a rare earth metal and a rare earth metal compound and the like can be given.

As the organic metal complex, at least one selected from an organic metal complex containing an alkali metal, an organic metal complex containing an alkaline earth metal and an organic metal complex containing a rare earth metal can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) and the like can be given.

As the alkaline earth metal, calcium (Ca) (work function: 2.9 eV), strontium (Sr) (work function: 2.0 eV or more and 2.5 eV or less), barium (Ba) (work function: 2.52 eV) and the like can be given.

As the rare earth metal, scandium (Sc), yttrium (Y), cerium (Ce), terbium (Tb), ytterbium (Yb) and the like can be given.

As the alkali metal compound, alkali oxides such as lithium oxide ($Li_2O$), cesium oxide ($Cs_2O$) and potassium oxide ($K_2O$), and alkali halides such as lithium fluoride (LiF), sodium fluoride (NaF), cesium fluoride (CsF), potassium fluoride (KF) or the like can be given. Among these, lithium fluoride (LiF), lithium oxide ($Li_2O$) and sodium fluoride (NaF) are preferable.

As the alkaline-earth metal compound, barium oxide (BaO), strontium oxide (SrO), calcium oxide (CaO), and mixtures thereof such as barium strontium acid ($Ba_xSr_{1-x}O$) (0<x<1) and barium calcium acid ($Ba_xCa_{1-x}O$) (0<x<1) can be given. Among these, BaO, SrO and CaO are preferable.

As the rare-earth metal compound, ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$) can be given. Among these, $YbF_3$, $ScF_3$ and $TbF_3$ are preferable.

The organic metal complexes are not particularly limited as long as they each contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

As the organic metal complex, 8-quinolinolate lithium and the like can be given.

When the electron-transporting layer contains at least one of an alkali metal and an alkaline earth metal, the content ratio thereof in the electron-transporting layer is preferably 0.1 to 50 mass %, more preferably 0.1 to 20 mass %, further preferably 1 to 10 mass %, and when the electron-transporting layer contains at least one of an organometallic complex containing an alkali metal and an organometallic complex containing an alkaline earth metal, the content ratio thereof in the electron-transporting layer is 1 to 99 mass %, and more preferably 10 to 90 mass %.

(Cathode)

For a cathode, it is preferable to use a metal having a small work function (specifically, 3.8 eV or less), an alloy, an electrically conductive compound, a mixture of those or the like. As specific examples of the cathode material, an element belonging to Group 1 or Group 2 of the periodic table of the elements, i.e., an alkali metal such as lithium (Li) or cesium (Cs), an alkaline earth metal such as magnesium (Mg), alloys containing the alkali metal and the alkaline earth metal (e.g. MgAg, AlLi) and a rare earth metal and an alloy containing the rare earth metal and the like can be given.

The above-mentioned organic electroluminescence device can be used in various electronic apparatuses. For example, it can be used in a planar luminous body such as a flat panel display of a wall-hanging TV, a backlight of a copier, a printer and a crystal liquid display, or a light source of instruments, a displaying board, sign lighting or the like. Further, the compound of the invention can be used not only in an organic EL device but also in the field of an electrophotographic photoreceptor, a photoelectric conversion element, a solar cell, an image sensor or the like.

EXAMPLES

Synthesis Example 1

[Synthesis of Compound (1)]

A synthesis scheme of compound (1) is shown below.

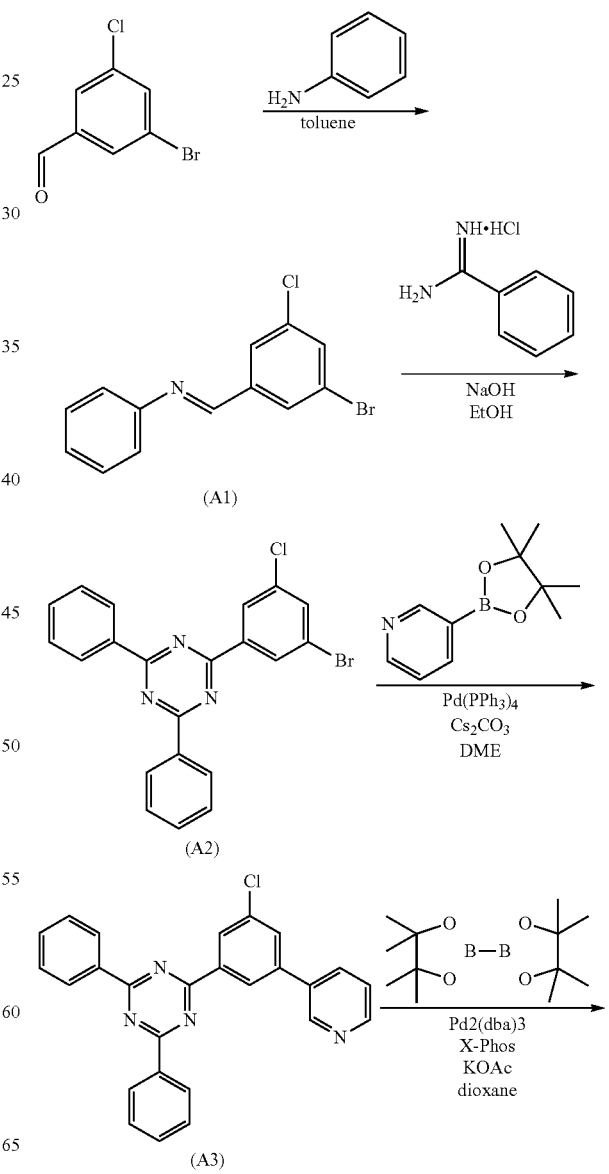

-continued

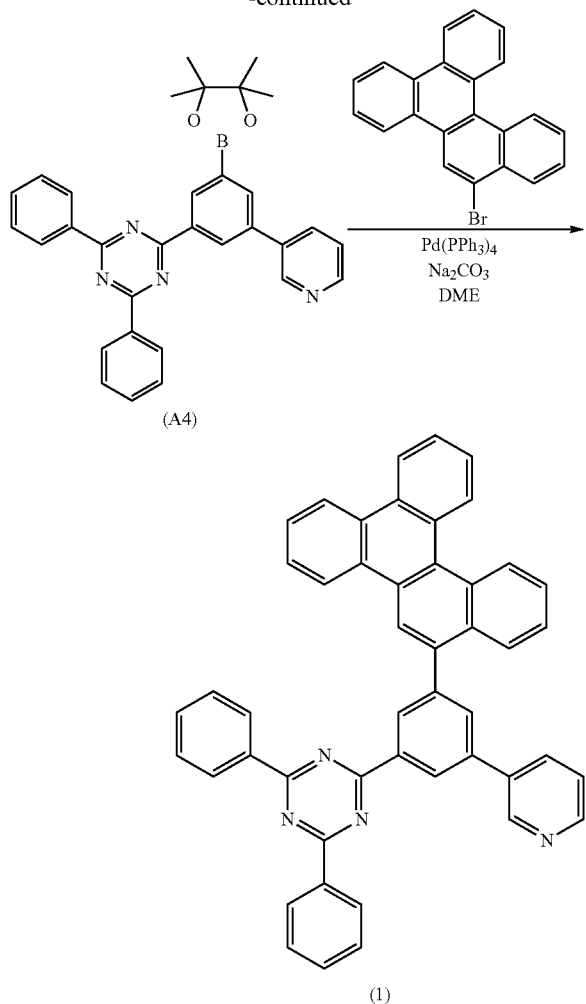

(A4)

(1)

(1-1) Synthesis of Intermediate (A1)

In an argon atmosphere, to a mixture of 3-bromo-5-chlorobenzaldehyde (745 g, 2.55 mol) and aniline (238 g, 2.55 mol), toluene (5.6 L) was added, and the resulting mixture was stirred at 111° C. while dehydrating for 18 hours. After completion of the reaction, the mixture was cooled to room temperature, the solution was concentrated under reduced pressure, whereby intermediate (A1) (702 g, 2.38 mol) was obtained. The yield of intermediate (A1) was 93%.

(1-2) Synthesis of Intermediate (A2)

In an argon atmosphere, to a mixture of intermediate (A1) (702 g, 2.38 mol) and benzamidine hydrochloride (746 g, 4.77 mol), ethanol (10.5 L) and sodium hydroxide (286 g, 7.15 mol) were added, and the resulting mixture was stirred at 79° C. for 20 hours. After completion of the reaction, the mixture was cooled to room temperature, and deposited crystals were collected by filtration. The collected crystals were purified by recrystallization method by using toluene, whereby intermediate (A2) (150 g, 0.357 mol) was obtained. The yield of the intermediate (A2) was 15%.

(1-3) Synthesis of Intermediate (A3)

In an argon atmosphere, dimethoxyethane (500 mL) was added to a mixture of intermediate (A2) (30.0 g, 71.0 mmol) and 3-(4,4,5,5-tetramethyl-1,3,2-dioxabora-2-yl)pyridine (21.8 g, 106 mmol) and tetrakis(triphenylphosphine)palladium(0) (4.92 g, 4.26 mmol) and cesium carbonate (34.7 g, 106 mmol), and the mixture was stirred at 75° C. for 9 hours. After completion of the reaction, the mixture was cooled to room temperature, and deposited crystals were separated by filtration. The collected crystals were dissolved in toluene and passed through silica gel column chromatography. The resulting solution was concentrated under reduced pressure, whereby intermediate (A3) (25.2 g, 59.9 mmol) was obtained. The yield of the intermediate (A3) was 84%.

(1-4) Synthesis of Intermediate (A4)

In an argon atmosphere, dioxane (600 mL) was added to a mixture of intermediate (A3) (25.2 g, 59.9 mmol), 4,4,4',4',5,5,5',5'-octamethyl-2,2'-bi(1,3,2-dioxaborolane) (18.3 g, 71.9 mmol), tris(dibenzylideneacetone)dipalladium (0) (1.10 g, 2.20 mmol), 2-dicyclohexylphosphino-2',4',6'-tri-isopropylbiphenyl (2.29 g, 4.79 mmol) and potassium acetate (120 g, 11.8 mmol), and the mixture was stirred under heating with reflux for 8 hours. After completion of the reaction, the mixture was cooled to room temperature, and toluene (300 mL) and water (300 mL) were added. After liquid separation, an organic layer was concentrated under reduced pressure. The concentrated organic layer was dissolved in dichloromethane and the solution was passed through silica gel column chromatography. The resulting solution was concentrated under reduced pressure, whereby intermediate (A4) (25.5 g, 49.7 mmol) was obtained. The yield of the intermediate (A4) was 83%.

(1-5) Synthesis of Compound (1)

In an argon atmosphere, dimethoxyethane (100 mL) was added to a mixture of intermediate (A4) (6.00 g, 11.7 mmol), 10-bromobenzo[g]chrysene (4.18 g, 11.7 mmol), tetrakis (triphenylphosphine)palladium (0) (0.541 g, 0.468 mmol) and a 2M aqueous solution of sodium carbonate (11.2 g, 35.1 mmol), and the mixture was stirred under heating with reflux for 5 hours. After completion of the reaction, the mixture was cooled to room temperature, and deposited crystals were collected by filtration. The collected crystals were washed with toluene, whereby compound (1) (8.10 g, 10.6 mmol) was obtained. The yield of compound (1) was 91%. As a result of mass spectrometry, the compound was found to have a m/e of 662, and was identified to be the above compound (1) (Exact mass: 662.25).

Synthesis Example 2

[Synthesis of Compound (2)]

(2-1) Synthesis of Intermediate (B1)

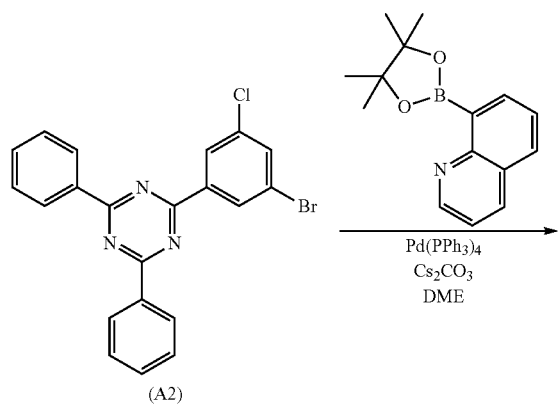

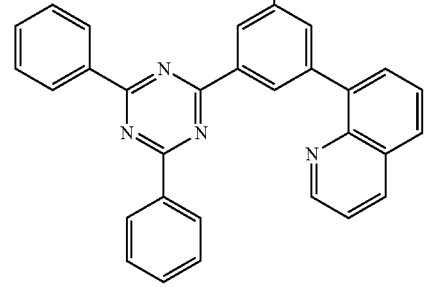

Synthesis was conducted in the same manner as in the synthesis of intermediate (A3), except that 8-(4,4,5,5-tetramethyl-1,3,2-dioxabolon-2-yl)quinoline was used instead of 3-(4,4,5,5-tetramethyl-1,3,2-dioxaborolan-2-yl)pyridine in the synthesis of intermediate (A3), whereby intermediate (B1) was obtained. The yield was 70%.

(2-2) Synthesis of Intermediate (B2)

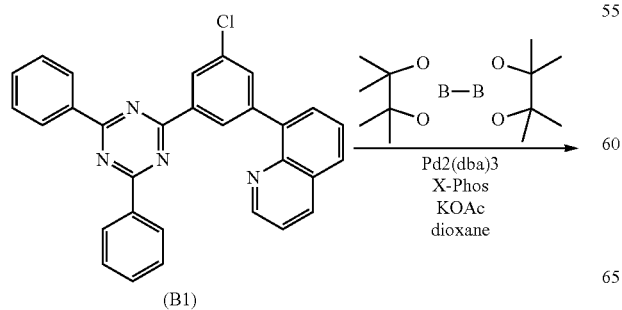

Synthesis was conducted in the same manner as in the synthesis of intermediate (A4), except that intermediate (B1) was used instead of intermediate (A3) in the synthesis of intermediate (A4), whereby intermediate (B2) was obtained. The yield was 79%.

(2-3) Synthesis of Compound (2)

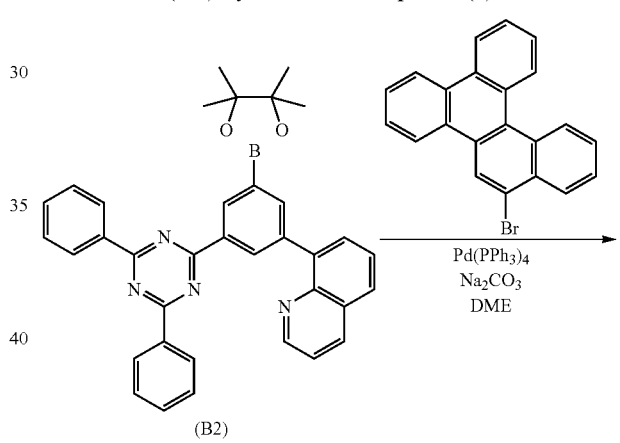

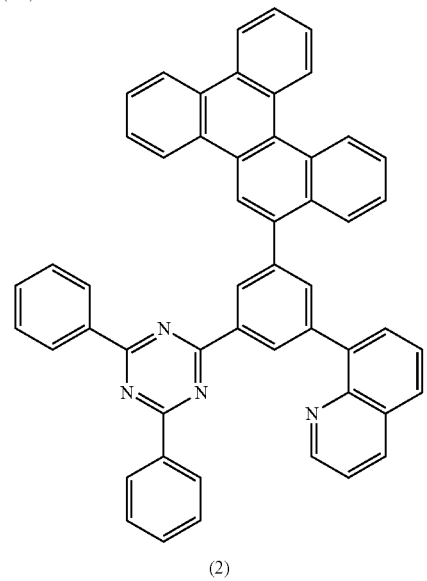

Synthesis was conducted in the same manner as in the synthesis of compound (1), except that intermediate (B2) was used instead of intermediate (A4) in the synthesis of compound (1), whereby compound (2) was obtained. The yield was 75%. As a result of mass spectrometry, the compound was found to have a m/e of 712, and was identified to be the above compound (2) (Exact mass: 712.26).

Synthesis Example 3

[Synthesis of Compound (3)]

(3-1) Synthesis of Intermediate (C1)

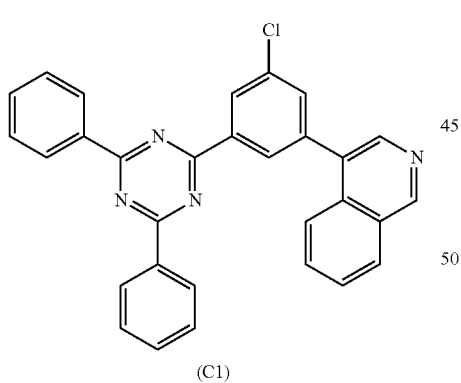

Synthesis was conducted in the same manner as in the synthesis of intermediate (A3), except that 4-isoquinolylboronic acid was used instead of 3-(4,4,5,5-tetramethyl-1,3,2-dioxabora-2-yl)pyridine in the synthesis of intermediate (A3), whereby intermediate (C1) was obtained. The yield was 81%.

(3-2) Synthesis of Intermediate (C2)

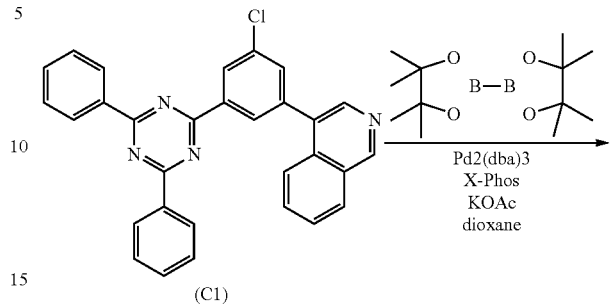

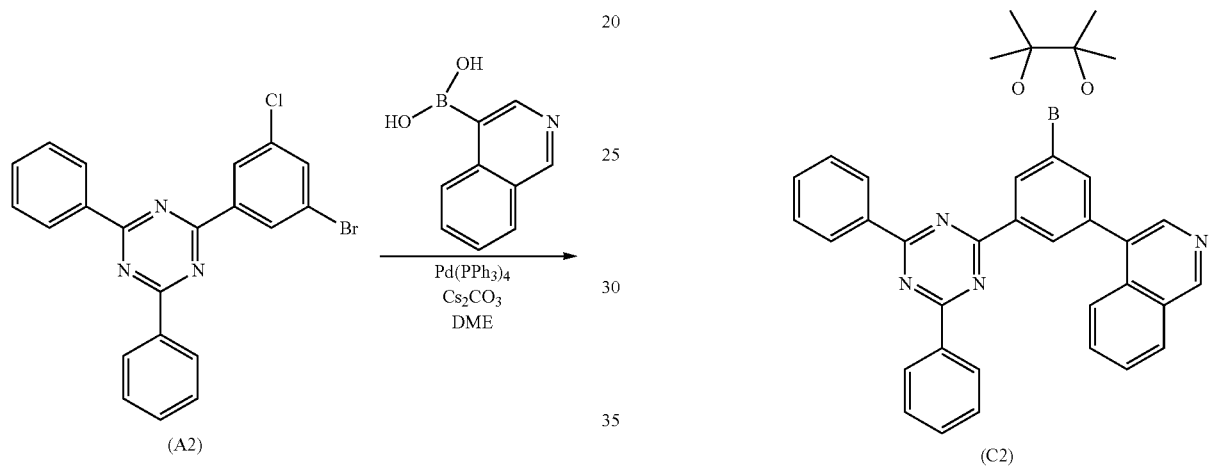

Synthesis was conducted in the same manner as in the synthesis of intermediate (A4) except that intermediate (C1) was used instead of intermediate (A3) in the synthesis of intermediate (A4), whereby intermediate (C2) was obtained. The yield was 81%.

(3-3) Synthesis of Compound (3)

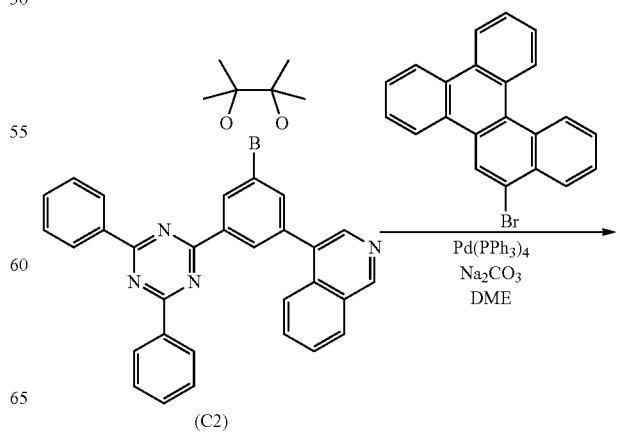

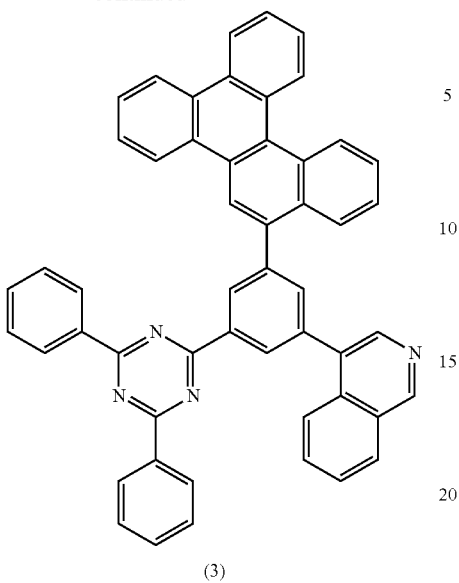

(3)

Synthesis was conducted in the same manner as in the synthesis of compound (1), except that intermediate (C2) was used instead of intermediate (A4) in the synthesis of compound (1), whereby compound (3) was obtained. The yield was 82%. As a result of mass spectrometry, the compound was found to have a m/e of 712, and was identified to be the above compound (3) (Exact mass: 712.26).

Synthesis Example 4

[Synthesis of Compound (4)]

(4-1) Synthesis of Compound (4)

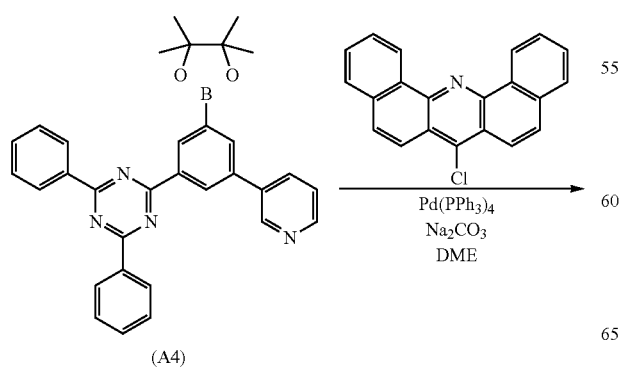

(A4)

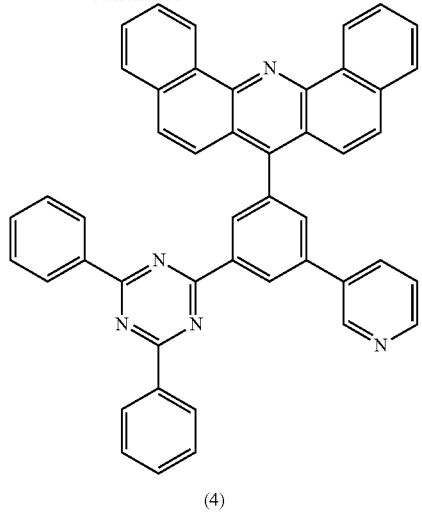

(4)

Synthesis was conducted in the same manner as in the synthesis of compound (1), except that 7-chlorodibenzo[c,h]acridine was used instead of 10-bromobenzo[g]chrysene in the synthesis of compound (1), whereby compound (4) was obtained. The yield was 82%. As a result of mass spectrometry, the compound was found to have a m/e of 663, and was identified to be the above compound (4) (Exact mass: 663.24).

Synthesis Example 5

[Synthesis of Compound (5)]

(5-1) Synthesis of Intermediate (D1)

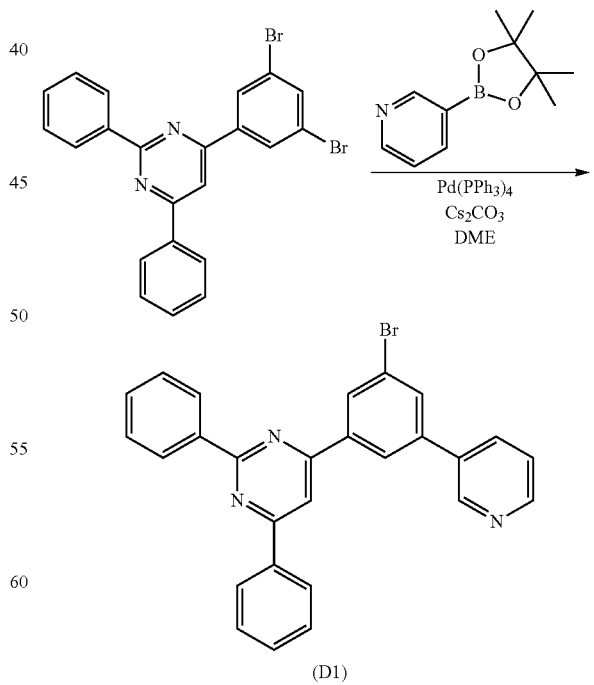

(D1)

Synthesis was conducted in the same manner as in the synthesis of intermediate (A3), except that 4-(3,5-dibromophenyl)-2,6-diphenylpyrimidine was used instead of intermediate (A2) in the synthesis of intermediate (A3), whereby intermediate (D1) was obtained. The yield was 85%.

(5-2) Synthesis of Intermediate (D2)

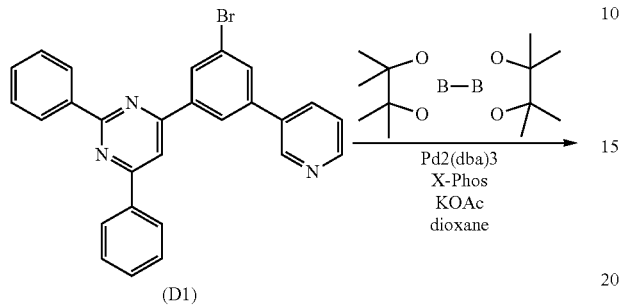

(D1)

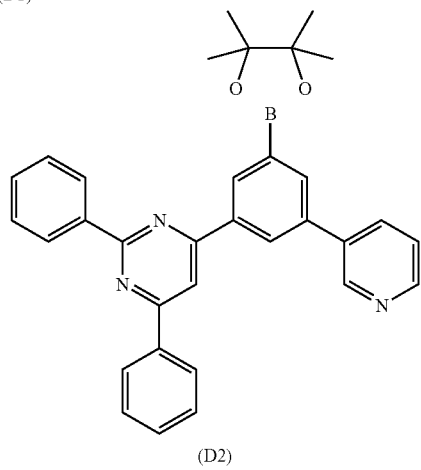

(D2)

Synthesis was conducted in the same manner as in the synthesis of intermediate (A4), except that intermediate (D1) was used instead of intermediate (A3) in the synthesis of intermediate (A4), whereby intermediate (D2) was obtained. The yield was 80%.

(5-3) Synthesis of Compound (5)

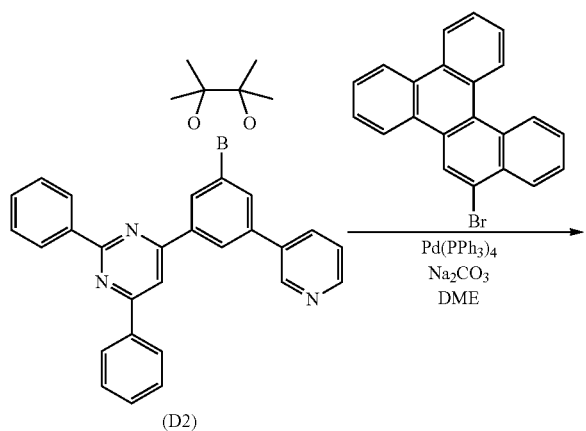

(D2)

-continued

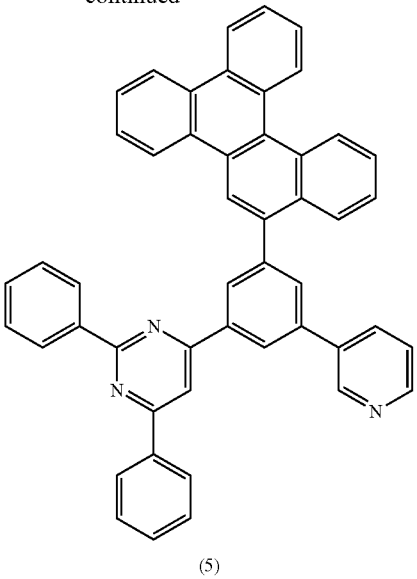

(5)

Synthesis was conducted in the same manner as in the synthesis of compound (1), except that intermediate (D2) was used instead of intermediate (A4) in the synthesis of compound (1), whereby compound (5) was obtained. The yield was 76%. As a result of mass spectrometry, the compound was found to have a m/e of 661, and was identified to be the above compound (5) (Exact mass: 661.25).

Example 1

[Fabrication and Evaluation of Organic EL Light Emitting Device]

A glass substrate with an ITO transparent electrode (anode) having a dimension of 25 mm×75 mm×1.1 mm in thickness (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound HI was deposited on the surface on which the transparent electrode lines had been formed so as to cover the transparent electrode, whereby a 5 nm-thick HI film was formed. The HI film functions as a hole-injecting layer.

Subsequent to formation of the HI film, compound HT-1 was deposited, whereby a 100 nm-thick HT-1 film was formed on the HI film. The HT-1 film functions as a first hole-transporting layer.

Subsequent to formation of the HT-1 film, compound HT-2 was deposited, whereby a 5 nm-thick HT-2 film was formed on the HT-1 film. The HT-2 film functions as a second hole-transporting layer.

On the HT-2 film, BH (host material) and BD (dopant material) were co-deposited such that the ratio of BD (weight ratio) became 3%, whereby a 15 nm-thick emitting layer was formed.

On this emitting layer, ET-1 was deposited, whereby a 5 nm-thick first electron-transporting layer was formed.

On the first electron-transporting layer, compound (1) and Liq were co-deposited such that the ratio (weight ratio) of compound (1) became 50%, whereby a 25 nm-thick second electron-transporting layer was formed.

Further, on the second electron-injecting layer, Liq was deposited, whereby a 1 nm-thick Liq film was formed.

Metal Al was deposited on this Liq film, whereby a 80 nm-thick metal cathode was formed, and as a result, an organic EL device was fabricated. The compounds used are shown below.

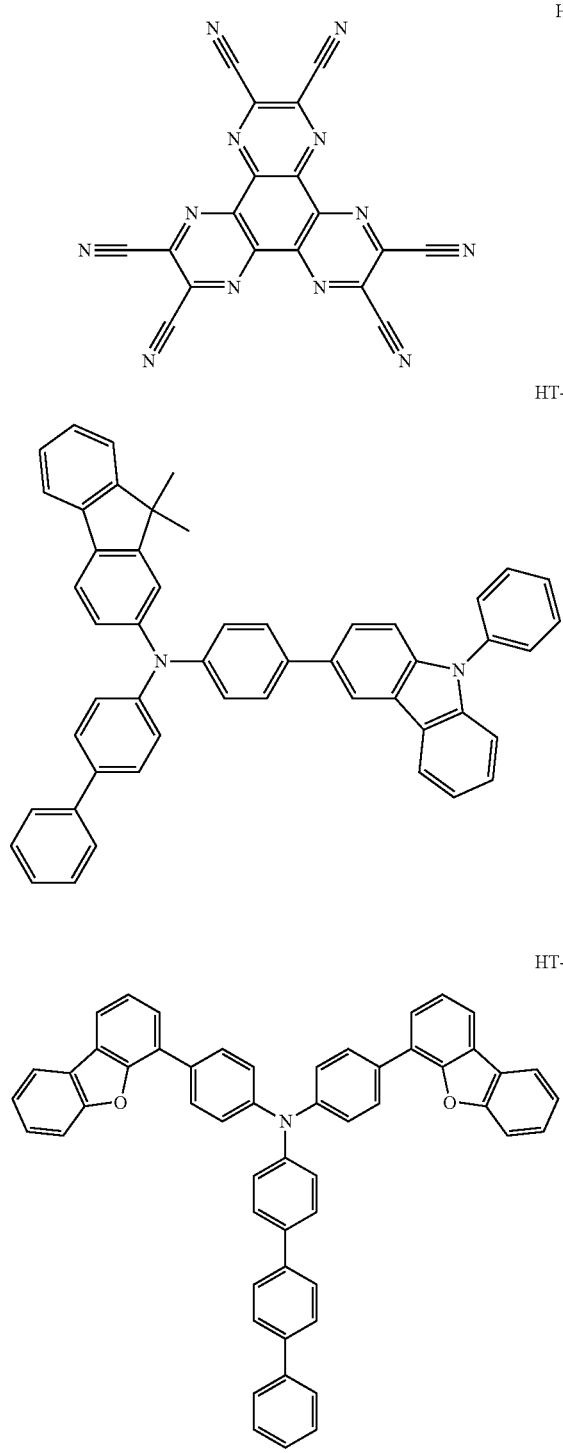

For the fabricated organic EL device, the driving voltage, the external quantum efficiency (EQE) and the device lifetime (LT97) were measured as follows. The results are shown in Table 1.

Driving Voltage (V)

A voltage (unit: V) when electric current was passed between the ITO transparent electrode and the metal Al cathode such that the current density became 10 mA/cm² was measured.

External Quantum Efficiency (EQE)

From a spectral radiance spectrum, an external quantum efficiency EQE (unit: %) was calculated on the assumption that lambassian radiation was conducted.

Device Lifetime

LT97 (a period of time taken until the initial luminance was reduced by 3%) was measured.

Comparative Example 1

An organic EL device was fabricated and evaluated in the same manner as in Example 1, except that the following comparative compound 1 was used instead of the compound (1) for the second electron-transporting layer. The results are shown in Table 1.

Comp. Compound 1

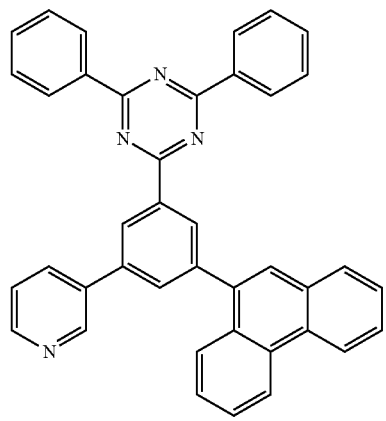

Examples 2 to 5 and Comparative Example 2

Organic EL devices were fabricated in the same manner as in Example 1, except that the following compounds (2) to (5) and Comparative Compound 2 were respectively used instead of compound (1) in the fabrication of an organic EL device in Example 1. For the obtained organic EL devices, and the driving voltage, the external quantum efficiency (EQE) and the device lifetime (LT97) were measured. The results are shown in Table 1.

Compound (2)

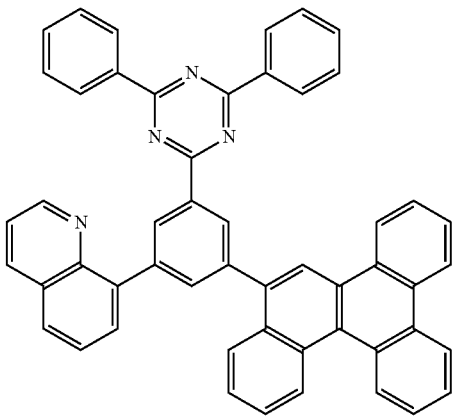

Compound (3)

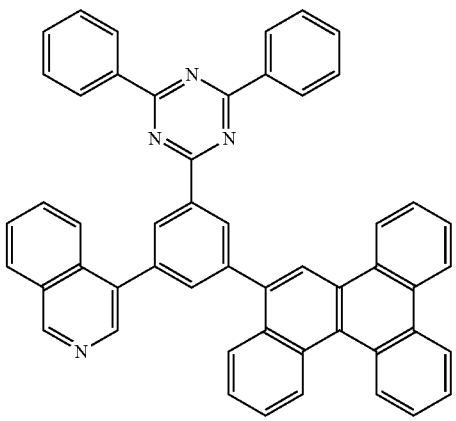

Compound (4)

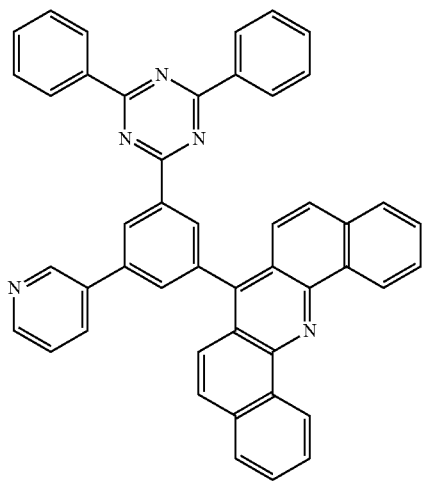

Compound (5)

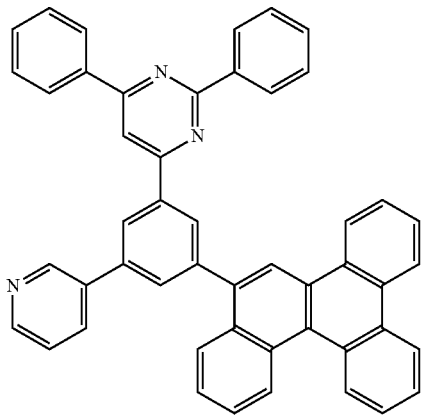

Comp. Compound 2

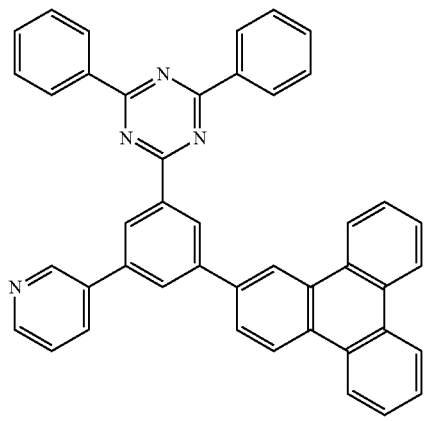

TABLE 1

| | Driving voltage (V) | External quantum efficiency (%) | LT97 (h) |
|---|---|---|---|
| Example 1 | 3.21 | 9.2 | 207 |
| Example 2 | 3.15 | 9.2 | 200 |
| Example 3 | 3.22 | 9.2 | 210 |
| Example 4 | 3.23 | 9.2 | 225 |
| Example 5 | 3.21 | 9.2 | 200 |
| Comp. Ex. 1 | 3.28 | 9.1 | 145 |
| Comp. Ex. 2 | 3.55 | 8.7 | 151 |

From the results shown in Table 1, it can be understood that the compound of the invention has excellent ability of improving the device lifetime.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A compound represented by the following formula (1):

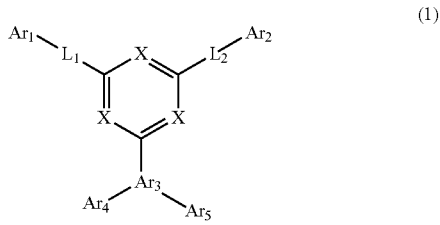

(1)

wherein in the formula (1), Xs are independently a nitrogen atom or CH, and at least two Xs are nitrogen atoms;

$Ar_1$ and $Ar_2$ are independently a substituted or unsubstituted aromatic hydrocarbon group including 6 to 30 ring carbon atoms or a substituted or unsubstituted aromatic heterocyclic group including 5 to 30 ring atoms;

$L_1$ and $L_2$ are independently a single bond or a substituted or unsubstituted aromatic hydrocarbon group including 6 to 30 ring carbon atoms;

$Ar_3$ is a substituted or unsubstituted aromatic hydrocarbon group including 6 to 15 ring carbon atoms;

$Ar_4$ is a substituted or unsubstituted 6-membered nitrogen-containing aromatic monocyclic group or a substituted or unsubstituted nitrogen-containing aromatic fused ring group in which two or more 6-membered rings are fused; and $Ar_5$ is represented by any of the following formulas (11) to (13):

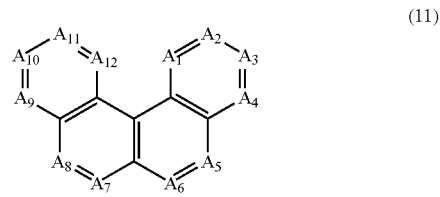

(11)

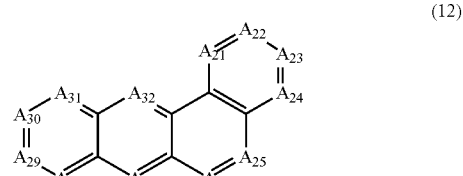

(12)

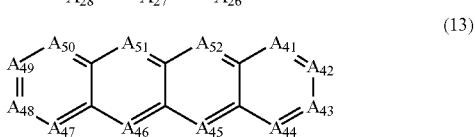

(13)

wherein in the formula (11), any one of $A_1$ to $A_{12}$ is a carbon atom that is used for bonding with $Ar_3$, any two of $A_1$ to $A_{12}$ that are not used for bonding with $Ar_3$ are $CR_1$s, the two $R_1$s are bonded with each other to form a substituted or unsubstituted 6-membered ring, and remaining $A_1$ to $A_{12}$ are independently a nitrogen atom or $CR_2$; and $R_2$ is a hydrogen atom or a substituent;

wherein in the formula (12), any one of $A_{21}$ to $A_{32}$ is a carbon atom that is used for bonding with $Ar_3$, any two of $A_{21}$ to $A_{32}$ that are not used for bonding with $Ar_3$ are $CR_1$s, the two $R_1$s are bonded with each other to form a substituted or unsubstituted 6-membered ring, and remaining $A_{21}$ to $A_{32}$ are independently a nitrogen atom or $CR_2$; and wherein in the formula (13), any one of $A_{41}$ to $A_{52}$ is a carbon atom that is used for bonding with $Ar_3$, any two of $A_{41}$ to $A_{52}$ that are not used for bonding with $Ar_3$ are $CR_1$s, the two $R_1$s are bonded with each other to form a substituted or unsubstituted 6-membered ring, and remaining $A_{41}$ to $A_{52}$ are independently a nitrogen atom or $CR_2$.

2. The compound according to claim 1, whrein $Ar_3$ is a substituted or unsubstituted benzene ring.

3. The compound according to claim 1 that is represented by the following formula (2):

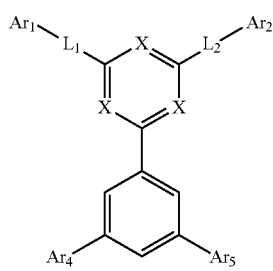

(2)

wherein in the formula (2), X, $Ar_1$, $Ar_2$, $L_1$, $L_2$, $Ar_4$ and $Ar_5$ are as defined in the formula (1).

4. The compound according to claim 1, wherein $Ar_5$ is represented by any of the following formulas (21) to (24):

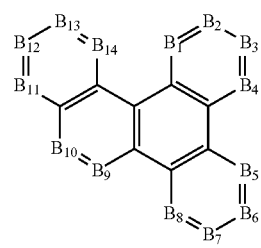

(21)

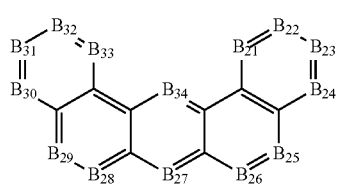

(22)

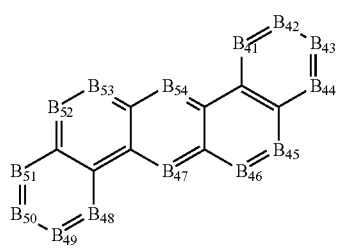

(23)

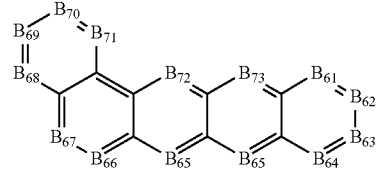

(24)

wherein in the formula (21), any one of $B_1$ to $B_{14}$ is a carbon atom that is used for bonding with $Ar_3$, and $B_1$ to $B_{14}$ that are not used for bonding with $Ar_3$ are independently a nitrogen atom or $CR_{11}$;

$R_{11}$ is a hydrogen atom or a substituent;

wherein in the formula (22), any one of $B_{21}$ to $B_{34}$ is a carbon atom that is used for bonding with $Ar_3$, and $B_{21}$ to $B_{34}$ that are not used for bonding with $Ar_3$ are independently a nitrogen atom or $CR_{11}$; and wherein in the formula (23), any one of $B_{41}$ to $B_{54}$ is a carbon atom that is used for bonding with $Ar_3$, and $B_{41}$ to $B_{54}$ that are not used for bonding with $Ar_3$ are independently a nitrogen atom or $CR_{11}$; and wherein in the formula (24), any one of $B_{61}$ to $B_{73}$ is a carbon atom that is used for bonding with $Ar_3$, and $B_{61}$ to $B_{73}$ that are not used for bonding with $Ar_3$ are independently a nitrogen atom or $CR_{11}$.

5. The compound according to claim 1, wherein $Ar_5$ is represented by any of the following formulas (31) to (37):

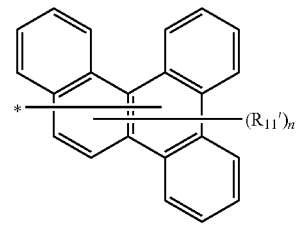

(31)

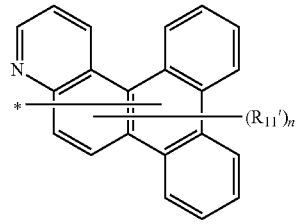

(32)

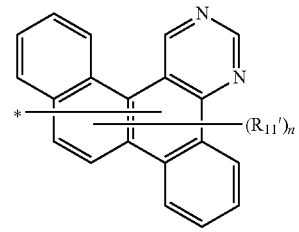

(33)

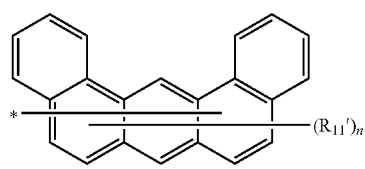

(34)

-continued

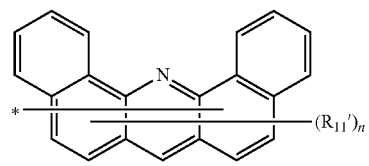
(35)

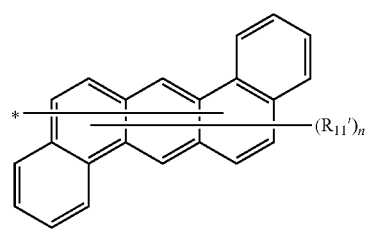
(36)

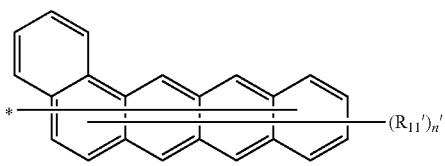
(37)

wherein in the formulas (31) to (37), $R_{11}'$ is a substituent, n is an integer of 0 to 13, n' is an integer of 0 to 12, * is a bonding position with $Ar_3$, $R_{11}'$ may be bonded at any position of the fused ring, and the bonding position with $Ar_3$ may be any position of the fused ring.

6. The compound according to claim 5, wherein $Ar_5$ is represented by the formula (31).

7. The compound according to claim 1, wherein $Ar_4$ is represented by any of the following formulas:

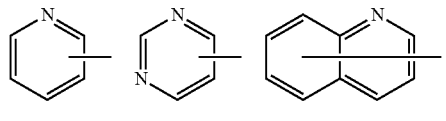

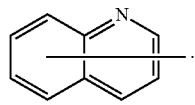

8. The compound according to claim 1, wherein $Ar_1$ and $Ar_2$ are independently a substituted or unsubstituted aromatic hydrocarbon group including 6 to 30 ring carbon atoms.

9. The compound according to claim 1, wherein $Ar_1$ and $Ar_2$ are independently a substituted or unsubstituted phenyl group, a substituted or unsubstituted biphenyl group, a substituted or unsubstituted naphthyl group or a substituted or unsubstituted fluorenyl group.

10. The compound according to claim 1, wherein $L_1$ and $L_2$ are independently a single bond or a substituted or unsubstituted phenylene group.

11. The compound according to claim 1, wherein all of the three Xs are nitrogen atoms.

12. The compound according to claim 1, that is a material for an organic electroluminescence device.

13. An organic electroluminescence device that comprises a cathode and an anode, and one or more organic layers including an emitting layer disposed between the cathode and the anode, wherein at least one layer of the organic layers comprises the compound according to claim 1.

14. The organic electroluminescence device according to claim 13 that further comprises an electron-transporting zone between the emitting layer and the cathode, wherein the electron-transporting zone has one or more organic layers and at least one layer of the organic layers comprises the compound.

15. The organic electroluminescence device according to claim 14, wherein at least one layer of the organic layers in the electron-transporting zone is an electron-transporting layer.

16. The organic electroluminescence device according to claim 14, wherein the electron-transporting zone comprises one or more selected from an electron-donating dopant and an organic metal complex.

17. The organic electroluminescence device according to claim 16, wherein the electron-transporting zone further comprises 8-quinolinolate lithium.

18. The organic electroluminescence device according to claim 13 that further comprises a hole-transporting layer between the anode and the emitting layer.

19. An electronic apparatus that is provided with the organic electroluminescence device according to claim 13.

* * * * *

UNITED STATES PATENT AND TRADEMARK OFFICE
CERTIFICATE OF CORRECTION

PATENT NO. : 10,461,258 B2
APPLICATION NO. : 15/389912
DATED : October 29, 2019
INVENTOR(S) : Takushi Shiomi and Masahiro Kawamura It is certified that error appears in the above-identified patent and that said Letters Patent is hereby corrected as shown below:

In the Claims

Claim 1, Column 66, Lines 44-51:
Please delete:

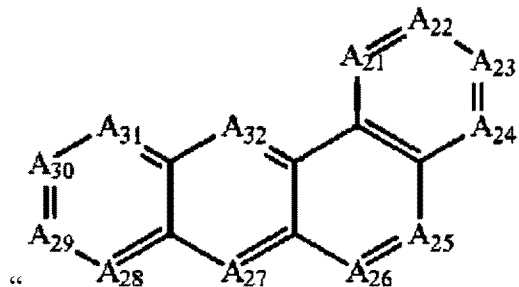

(12)

" "

Please replace with:

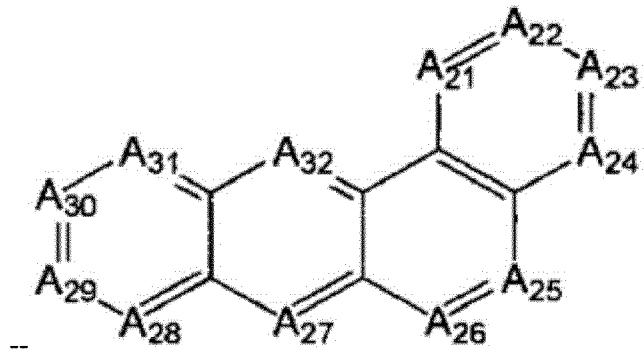

(12)

-- --

Claim 2, Column 67, Line 14:
Please delete:
"The compound according to claim 1, whrein $Ar_3$ is a"

Signed and Sealed this
Eighteenth Day of February, 2020

Andrei Iancu
*Director of the United States Patent and Trademark Office*

Please replace with:
--The compound according to claim 1, wherein Ar₃ is a--
Claim 7, Column 69, Lines 41-45:
Please delete:
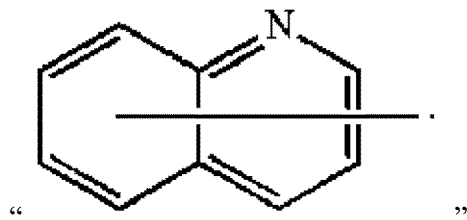
" "
Please replace with:
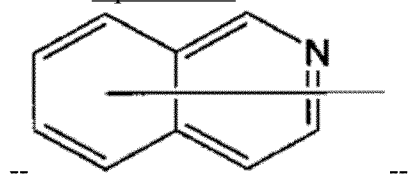
-- --